(12) United States Patent
Costella et al.

(10) Patent No.: US 10,272,224 B2
(45) Date of Patent: Apr. 30, 2019

(54) HUFF COUGH SIMULATION DEVICE

(71) Applicant: Trudell Medical International, London (CA)

(72) Inventors: Stephen Costella, London (CA); Adam Meyer, London (CA); Peter Scarrott, London (CA)

(73) Assignee: Trudell Medical International, London, Ontario (CA)

( * ) Notice: Subject to any disclaimer, the term of this patent is extended or adjusted under 35 U.S.C. 154(b) by 937 days.

(21) Appl. No.: 14/329,011

(22) Filed: Jul. 11, 2014

(65) Prior Publication Data

US 2015/0013671 A1 Jan. 15, 2015

Related U.S. Application Data

(60) Provisional application No. 61/845,689, filed on Jul. 12, 2013.

(51) Int. Cl.
*A61M 16/00* (2006.01)
*A61M 16/20* (2006.01)
(Continued)

(52) U.S. Cl.
CPC ........ *A61M 16/201* (2014.02); *A61M 15/002* (2014.02); *A61M 15/0086* (2013.01); *A61M 16/0009* (2014.02); *A61M 16/14* (2013.01); *A61M 16/208* (2013.01); *A61M 15/009* (2013.01); *A61M 15/0021* (2014.02);
(Continued)

(58) Field of Classification Search
CPC .............. A61M 15/00; A61M 15/0001; A61M 15/002; A61M 15/0013; A61M 16/201; A61M 16/14; A61M 15/009; A61M 15/0086; A61M 15/0091; A61M 16/00
See application file for complete search history.

(56) References Cited

U.S. PATENT DOCUMENTS 393,869 A  12/1888  Warren
938,808 A  11/1909  Yount
(Continued)

FOREIGN PATENT DOCUMENTS

EP   0 372 148 A1   6/1990
EP   0 678 306 A2   10/1995
(Continued)

OTHER PUBLICATIONS

PCT International Search Report for PCT/CA2014/000562 dated Oct. 16, 2014.
(Continued)

*Primary Examiner* — Gregory A Anderson
*Assistant Examiner* — Ned T Heffner
(74) *Attorney, Agent, or Firm* — Brinks Gilson & Lione

(57) ABSTRACT

A respiratory treatment device having an inlet configured to receive exhaled air into the device and an outlet configured to permit exhaled air to exit the device. A blocking member is moveable between a closed position where the flow of air through the device is restricted, and an open position where the flow of air through the device is less restricted. A biasing member is configured to bias the blocking member toward the closed position, wherein a level of bias decreases as the blocking member moves from the closed position to the open position.

22 Claims, 30 Drawing Sheets

(51) Int. Cl.
*A61M 16/14* (2006.01)
*A61M 15/00* (2006.01)
(52) U.S. Cl.
CPC .............. *A61M 2016/0027* (2013.01); *A61M 2202/064* (2013.01); *A61M 2205/0272* (2013.01)

(56) References Cited

U.S. PATENT DOCUMENTS

| | | | |
|---|---|---|---|
| 2,670,739 A | 3/1954 | NcNeill | |
| 2,918,917 A | 12/1959 | Emerson | |
| 3,486,502 A | 12/1969 | Wilson | |
| 3,710,780 A | 1/1973 | Milch | |
| 3,908,987 A | 9/1975 | Boehringer | |
| 4,054,134 A | 10/1977 | Kritzer | |
| 4,062,358 A | 12/1977 | Kritzer | |
| 4,182,366 A | 1/1980 | Boehringer | |
| 4,198,969 A | 4/1980 | Virag | |
| 4,210,174 A | 7/1980 | Eross | |
| 4,221,381 A * | 9/1980 | Ericson | A63B 23/18 482/13 |
| 4,226,233 A | 10/1980 | Kritzer | |
| 4,231,375 A | 11/1980 | Boehringer et al. | |
| 4,267,832 A | 5/1981 | Hakkinen | |
| 4,275,722 A | 6/1981 | Sorensen | |
| 4,298,023 A | 11/1981 | McGinnis | |
| 4,327,740 A | 5/1982 | Shuman | |
| 4,403,616 A | 9/1983 | King | |
| 4,436,090 A | 3/1984 | Darling | |
| 4,470,412 A | 9/1984 | Nowacki et al. | |
| 4,473,082 A * | 9/1984 | Gereg | A63B 23/18 128/205.17 |
| 4,487,207 A * | 12/1984 | Fitz | A63B 23/18 482/1 |
| 4,533,137 A * | 8/1985 | Sonne | A63B 23/18 128/207.16 |
| 4,601,465 A * | 7/1986 | Roy | A63B 23/18 128/207.16 |
| 4,611,591 A | 9/1986 | Inui et al. | |
| 4,635,631 A | 1/1987 | Izumi | |
| 4,651,731 A | 3/1987 | Vicenzi et al. | |
| 4,739,987 A | 4/1988 | Nicholson | |
| 4,770,413 A | 9/1988 | Green | |
| 4,854,574 A * | 8/1989 | Larson | A63B 23/18 128/200.24 |
| 4,973,047 A | 11/1990 | Norell | |
| 4,981,295 A | 1/1991 | Belman et al. | |
| 5,018,517 A | 5/1991 | Liardet | |
| 5,042,467 A | 8/1991 | Foley | |
| 5,065,746 A | 11/1991 | Steen | |
| 5,190,036 A | 3/1993 | Linder | |
| 5,193,529 A | 3/1993 | Labaere | |
| 5,345,930 A | 9/1994 | Cardinal et al. | |
| 5,381,789 A | 1/1995 | Marquardt | |
| 5,397,337 A | 3/1995 | Jaeger et al. | |
| 5,451,190 A * | 9/1995 | Liardet | A63B 23/18 128/200.24 |
| 5,479,920 A | 1/1996 | Piper et al. | |
| 5,540,220 A | 7/1996 | Gropper et al. | |
| 5,569,122 A | 10/1996 | Cegla | |
| 5,570,682 A | 11/1996 | Johnson | |
| 5,598,839 A | 2/1997 | Niles et al. | |
| 5,613,489 A | 3/1997 | Miller | |
| 5,645,049 A | 7/1997 | Foley et al. | |
| 5,647,345 A | 7/1997 | Saul | |
| 5,655,520 A | 8/1997 | Howe | |
| 5,658,221 A | 8/1997 | Hougen | |
| 5,791,339 A | 8/1998 | Winter | |
| 5,829,429 A | 11/1998 | Hughes | |
| 5,848,588 A | 12/1998 | Foley et al. | |
| 5,857,957 A | 1/1999 | Lin | |
| 5,862,802 A | 1/1999 | Bird | |
| 5,890,998 A * | 4/1999 | Hougen | A61M 16/0006 482/13 |
| 5,893,361 A | 4/1999 | Hughes | |
| 5,896,857 A * | 4/1999 | Hely | A62B 9/02 128/203.11 |
| 5,899,832 A | 5/1999 | Hougen | |
| 5,910,071 A | 6/1999 | Hougen | |
| 5,925,831 A | 7/1999 | Storsved | |
| 6,026,807 A | 2/2000 | Puderbaugh et al. | |
| 6,044,841 A | 4/2000 | Verdun et al. | |
| 6,058,932 A | 5/2000 | Hughes | |
| 6,066,101 A | 5/2000 | Johnson | |
| 6,083,141 A | 7/2000 | Hougen | |
| 6,089,105 A | 7/2000 | Ricciardelli | |
| 6,102,038 A | 8/2000 | DeVries | |
| 6,167,881 B1 | 1/2001 | Hughes | |
| 6,176,235 B1 | 1/2001 | Benarrouch et al. | |
| D440,651 S | 4/2001 | Foran | |
| 6,240,917 B1 | 6/2001 | Andrade | |
| 6,253,766 B1 | 7/2001 | Niles | |
| 6,293,279 B1 | 9/2001 | Schmidt et al. | |
| 6,340,025 B1 | 1/2002 | Van Brunt | |
| 6,345,617 B1 | 2/2002 | Engelbreth et al. | |
| 6,412,481 B1 | 7/2002 | Bienvenu et al. | |
| 6,500,095 B1 | 12/2002 | Hougen | |
| 6,539,938 B2 | 4/2003 | Weinstein et al. | |
| 6,557,549 B2 | 5/2003 | Schmidt et al. | |
| 6,581,595 B1 | 6/2003 | Murdock et al. | |
| 6,581,596 B1 | 6/2003 | Truitt | |
| 6,581,598 B1 | 6/2003 | Foran et al. | |
| 6,581,600 B2 | 6/2003 | Bird | |
| 6,595,203 B1 | 7/2003 | Bird | |
| 6,606,989 B1 | 8/2003 | Brand | |
| 6,615,831 B1 | 9/2003 | Truitt | |
| 6,631,721 B1 | 10/2003 | Salter et al. | |
| 6,659,100 B2 | 12/2003 | O'Rourke | |
| 6,702,769 B1 | 3/2004 | Fowler-Hawkins | |
| 6,708,690 B1 | 3/2004 | Hete et al. | |
| 6,708,691 B1 | 3/2004 | Hayek | |
| 6,726,598 B1 * | 4/2004 | Jarvis | A63B 23/18 128/200.24 |
| D490,519 S | 5/2004 | Pelerossi et al. | |
| 6,776,159 B2 | 8/2004 | Pelerossi et al. | |
| 6,848,443 B2 | 2/2005 | Schmidt et al. | |
| 6,851,425 B2 | 2/2005 | Jaffre | |
| 6,860,265 B1 | 3/2005 | Emerson | |
| 6,889,687 B1 * | 5/2005 | Olsson | A61M 15/0091 128/200.14 |
| 6,904,906 B2 | 6/2005 | Salter | |
| 6,923,181 B2 | 8/2005 | Tuck | |
| 6,929,007 B2 | 8/2005 | Emerson | |
| 6,984,214 B2 | 1/2006 | Fowler-Hawkins | |
| 7,059,324 B2 | 6/2006 | Pelerossi et al. | |
| 7,096,866 B2 | 8/2006 | Be'eri et al. | |
| 7,134,434 B2 | 11/2006 | Truitt et al. | |
| 7,165,547 B2 | 1/2007 | Truitt et al. | |
| 7,188,621 B2 | 3/2007 | DeVries | |
| 7,191,776 B2 | 3/2007 | Niles | |
| 7,191,780 B2 | 3/2007 | Faram | |
| 7,214,170 B2 | 5/2007 | Sumners et al. | |
| 7,383,740 B2 | 6/2008 | Krasilchikov et al. | |
| 7,617,821 B2 | 11/2009 | Hughes | |
| 7,699,054 B2 | 4/2010 | Pelerossi et al. | |
| 7,717,847 B2 | 5/2010 | Smith | |
| 7,771,472 B2 | 8/2010 | Hendricksen | |
| 7,779,841 B2 | 8/2010 | Dunsmore et al. | |
| 7,798,148 B2 | 9/2010 | Doshi | |
| 7,856,979 B2 | 12/2010 | Doshi | |
| 7,909,033 B2 | 3/2011 | Faram | |
| 7,927,293 B2 | 4/2011 | Ignagni et al. | |
| 8,006,922 B2 | 8/2011 | Katzer | |
| 8,025,051 B2 | 9/2011 | Dagsland | |
| 8,025,054 B2 | 9/2011 | Dunsmore et al. | |
| 8,043,236 B2 | 10/2011 | Goldshtein et al. | |
| 8,051,854 B2 | 11/2011 | Faram | |
| RE43,174 E | 2/2012 | Schmidt et al. | |
| 8,118,024 B2 | 2/2012 | DeVries et al. | |
| 8,118,713 B2 | 2/2012 | Foley et al. | |
| 8,225,785 B2 | 7/2012 | Richards et al. | |
| 8,251,876 B2 * | 8/2012 | Boerst | A63B 21/00196 128/203.12 |

(56) References Cited

U.S. PATENT DOCUMENTS

| | | | |
|---|---|---|---|
| 8,327,849 B2 | 12/2012 | Grychowski et al. | |
| 8,460,223 B2 | 6/2013 | Huster et al. | |
| 8,469,029 B2 | 6/2013 | Brown et al. | |
| 8,485,179 B1 | 7/2013 | Meyer | |
| 8,539,951 B1* | 9/2013 | Meyer | A61M 16/0096 |
| | | | 128/200.24 |
| 8,985,111 B2 | 3/2015 | Grychowski et al. | |
| D731,050 S | 6/2015 | Meyer | |
| 9,149,589 B2 | 10/2015 | Meyer et al. | |
| 9,220,855 B2 | 12/2015 | Meyer | |
| 2003/0036786 A1* | 2/2003 | Duren | A47C 21/04 |
| | | | 607/96 |
| 2004/0016428 A9 | 1/2004 | Lurie | |
| 2007/0259759 A1 | 11/2007 | Sumners et al. | |
| 2008/0053452 A1* | 3/2008 | Brown | A63B 21/00196 |
| | | | 128/207.12 |
| 2008/0053456 A1 | 3/2008 | Brown et al. | |
| 2008/0096728 A1* | 4/2008 | Foley | A63B 23/18 |
| | | | 482/13 |
| 2009/0241949 A1 | 10/2009 | Smutney et al. | |
| 2010/0101573 A1* | 4/2010 | Foley | A61M 16/208 |
| | | | 128/203.15 |
| 2010/0139655 A1 | 6/2010 | Genosar | |
| 2010/0282253 A1* | 11/2010 | Newman, Jr. | A61M 16/208 |
| | | | 128/202.22 |
| 2010/0307487 A1 | 12/2010 | Dunsmore et al. | |
| 2012/0097164 A1 | 4/2012 | Rozario et al. | |
| 2012/0285460 A1 | 11/2012 | Smith et al. | |
| 2012/0304988 A1* | 12/2012 | Meyer | A61M 16/208 |
| | | | 128/203.12 |
| 2013/0118498 A1* | 5/2013 | Robitaille | A61M 16/0075 |
| | | | 128/205.16 |
| 2013/0133649 A1 | 5/2013 | Grychowski et al. | |
| 2013/0184619 A1 | 7/2013 | Von Hollen et al. | |
| 2013/0220325 A1* | 8/2013 | Davis | A61M 16/00 |
| | | | 128/204.23 |
| 2013/0284171 A1 | 10/2013 | Adam et al. | |
| 2013/0312746 A1 | 11/2013 | Grychowski | |
| 2014/0041657 A1 | 2/2014 | Meyer | |
| 2014/0150790 A1 | 6/2014 | Meyer | |
| 2015/0053209 A1 | 2/2015 | Meyer et al. | |
| 2015/0151060 A1 | 2/2015 | Grychowski et al. | |
| 2015/0224269 A1 | 8/2015 | Alizoti et al. | |
| 2015/0297848 A1 | 10/2015 | Meyer et al. | |
| 2015/0374939 A1 | 12/2015 | Meyer et al. | |
| 2016/0136369 A1 | 5/2016 | Meyer et al. | |

FOREIGN PATENT DOCUMENTS

| | | |
|---|---|---|
| EP | 1 464 357 A1 | 10/2004 |
| EP | 1 435 251 B1 | 6/2006 |
| EP | 1 103 287 B1 | 6/2007 |
| EP | 1 897 576 A1 | 3/2008 |
| EP | 1 908 489 A1 | 4/2008 |
| EP | 2444114 | 4/2012 |
| EP | 2455137 | 5/2012 |
| GB | 2 425 488 A | 11/2006 |
| WO | WO 1989/03707 A1 | 5/1989 |
| WO | WO 1996/40376 | 12/1996 |
| WO | WO 1999/16490 | 4/1999 |
| WO | WO 2000/27455 | 5/2000 |
| WO | WO 01/89618 A1 | 11/2001 |
| WO | WO 2007/061648 A3 | 5/2007 |
| WO | WO 2007/119104 A3 | 10/2007 |
| WO | WO 2008/063966 A1 | 5/2008 |
| WO | WO 2008/122045 A1 | 10/2008 |
| WO | WO 2009/131965 | 10/2009 |
| WO | WO 2011/010279 A1 | 1/2011 |
| WO | WO 2011/058470 | 5/2011 |
| WO | WO 2012/038864 A2 | 3/2012 |
| WO | WO 2012/042255 A1 | 4/2012 |
| WO | WO 2013/001398 A1 | 1/2013 |
| WO | WO 2014/202923 | 12/2014 |
| WO | WO 2014/202924 | 12/2014 |
| WO | WO 2014/203115 | 12/2014 |
| WO | WO 2016/012740 | 1/2016 |

OTHER PUBLICATIONS

PCT Written Opinion for PCT/CA2014/000562 dated Oct. 16, 2014.
Supplemental European Search Report for related application No. 14822301.9; dated Feb. 21, 2017. (8 pgs).
U.S. Appl. No. 13/996,759, filed Aug. 14, 2013, Meyer.
U.S. Appl. No. 14/329,011, filed Jul. 11, 2014, Costella, et al.
U.S. Appl. No. 14/674,494, filed Mar. 31, 2015, Meyer et al.
U.S. Appl. No. 29/524,678, filed Apr. 22, 2015, Meyer et al.
U.S. Appl. No. 29/538,317, filed Sep. 2, 2015, Engelbreth et al.
U.S. Appl. No. 29/538,323, filed Sep. 2, 2015, Engelbreth et al.
Web page entitled Bronchial Hygiene, acapella Vibratory PEP Therapy System accessed from http://www.smiths-medical.com/catalog/bronchial-hygiene/acapella/acapella.html on Jul. 7, 2009.
Web page entitled Thayer Quake accessed from http://www.thayermedical.com/quake.htm on Jul. 7, 2009.
Human growth hormone, cortisol, and acid-base balance changes after hyperventilation and breath-holding; PubMed—indexed for MEDLINE; Int J Sports Med., Dec. 1986; 7(6):311-5, Djarova T.
Bosco C, Cardinale M. & Tsarpela O (1999). Influence of vibration on mechanical power and electromyogram activity in human arm flexor muscles. Eur J Appl Physiol 79, 306-311.
David Sumners; Power Breathing and Strength; http://EzineArticles.com/972576 Published: Feb. 7, 2008.
Good Vibrations blog; http://vibrotraining.blogspot.com, Earliest posting Jan. 17, 2008.
Breathtaking News; More Youbreathe; Aug. 10, 2007.
PCT International Search Report for PCT/IB2012/001089, dated Oct. 5, 2012.
PCT International Written Opinion for PCT/IB2012/001089, dated Oct. 5, 2012.

* cited by examiner

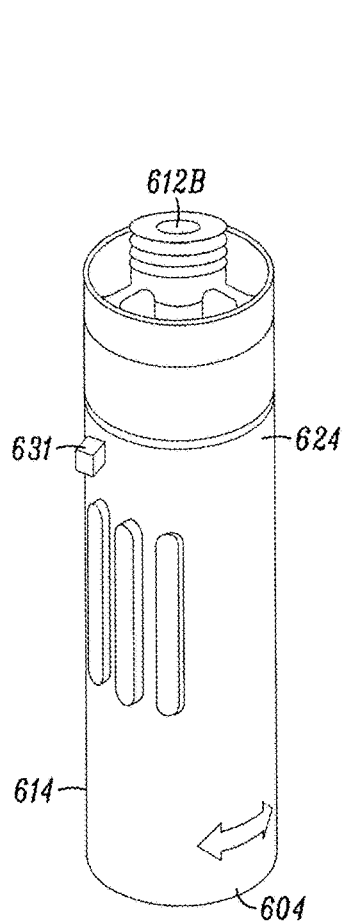
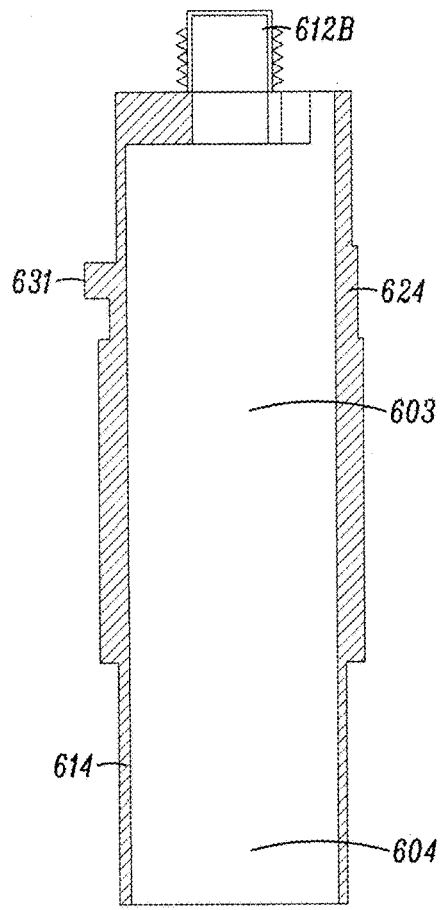
FIG. 29A        FIG. 29B
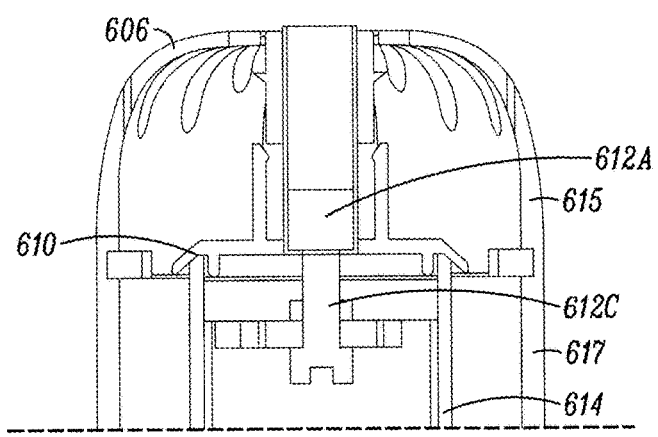
FIG. 30

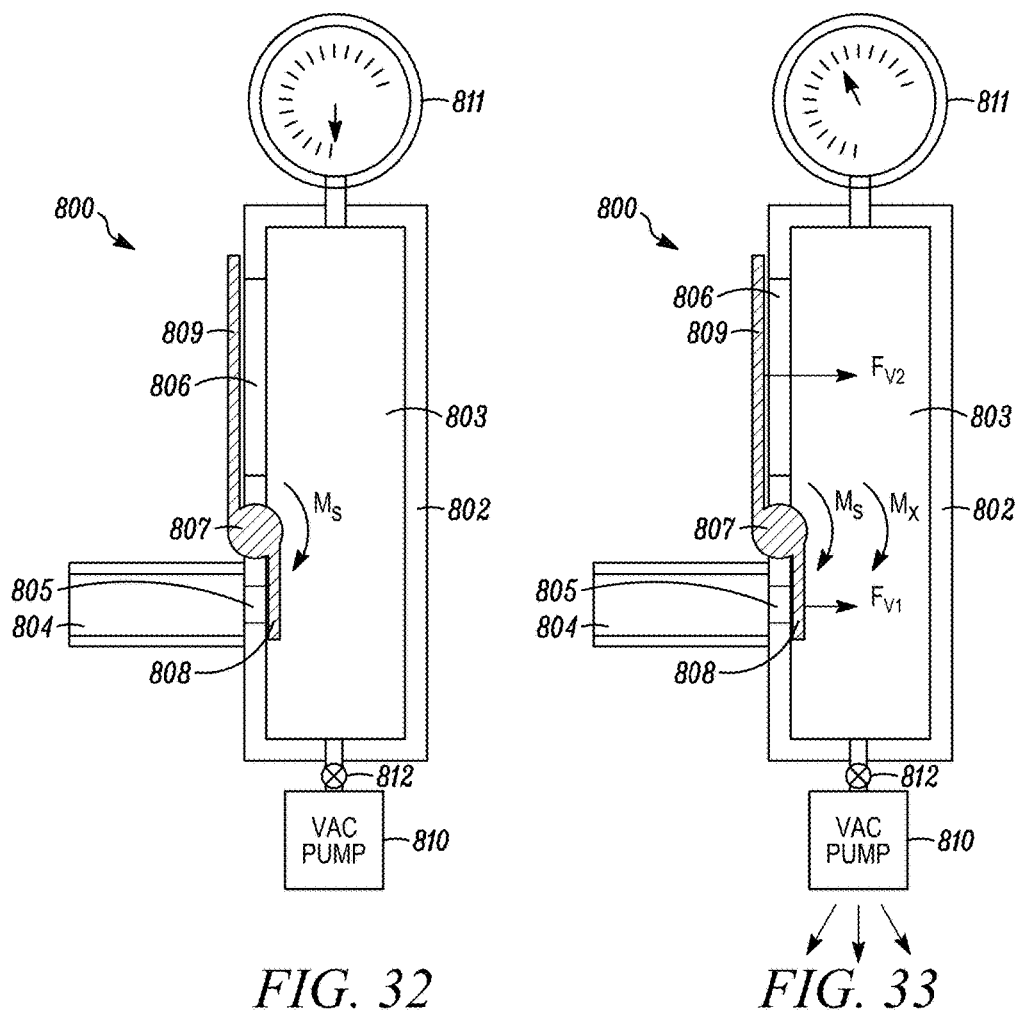
*FIG. 32*  *FIG. 33*

HUFF COUGH SIMULATION DEVICE

RELATED APPLICATION

This application claims the benefit of U.S. Provisional Application No. 61/845,689, filed on Jul. 12, 2013, which is incorporated herein by reference.

TECHNICAL FIELD

The present disclosure relates to a respiratory treatment device, and in particular, to a Huff Cough simulation device.

BACKGROUND

The Huff Cough is an effective technique for clearance of pulmonary secretions from the airways. It is often utilized in the treatment of COPD, or Chronic Obstructive Pulmonary Disease, although it may also be useful in other respiratory treatments. In general, the Huff Cough involves a patient using his or her diaphragm to breathe in slowly, holding the breath for two to three seconds, and forcing the breath out of his or her mouth in one quick burst of air, making sure the back of the throat is kept open. This technique is typically repeated multiple times during a single treatment. The length and force of the breath may be varied in order to treat different portions of a patient's airways.

Despite its efficacy, the Huff Cough may be difficult for some populations to effectively perform, requiring coaching from respiratory professionals. To that end, a user-friendly Huff Cough simulation device that provides physicians and patients with improved control over the treatment is desirable.

BRIEF SUMMARY

In one aspect, a respiratory treatment device includes an inlet configured to receive exhaled air into the device and an outlet configured to permit exhaled air to exit the device. A blocking member is moveable between a closed position where the flow of air through the device is restricted, and an open position where the flow of air through the device is less restricted. A biasing member is configured to bias the blocking member toward the closed position. A level of bias decreases as the blocking member moves from the closed position to the open position.

In another aspect, a respiratory treatment device includes an inlet configured to receive exhaled air into the device and an outlet configured to permit exhaled air to exit the device. A blocking member is moveable between a closed position where the flow of air through the device is restricted, and an open position where the flow of air through the device is less restricted. A biasing member is configured to maintain the blocking member in the closed position until a threshold exhalation pressure is reached in the device. The blocking member is maintained in the open position once the blocking member moves to the open position. In another aspect, a level of bias may decrease as the blocking member moves from the closed position to the open position. The blocking member may be moveable form the open position to the closed position by a user.

In a further aspect, the biasing member may include a pair of magnets. The pair of magnets may be configured to attract one another. A distance between a first magnet and a second magnet of the pair of magnets may be selectively adjustable when the blocking member is in the closed position. A magnet of the pair of magnets may be positioned on the blocking member.

In a further aspect, the biasing member may include a magnet and a metal object.

In a further aspect, the biasing member may include a latch.

In a further aspect, the blocking member may move from the closed position to the open position in response to a threshold exhalation pressure in the device.

In a further aspect, the blocking member may be a cap covering the outlet. Alternatively, the blocking member may be a piston positioned in the device.

In a further aspect, the inlet may be in fluid communication with a generally circular mouthpiece. The generally circular mouthpiece may be approximately one inch in diameter.

In another aspect, a method of performing respiratory treatment includes receiving a flow of exhaled air into a device having an inlet configured to receive exhaled air into the device and an outlet configured to permit exhaled air to exit the device; blocking the flow of exhaled air through the device by biasing a blocking member toward a closed position, where the flow of air through the device is restricted; decreasing the bias in response to a threshold pressure in the device; and, unblocking the flow of exhaled air through the device by moving the blocking member to an open position, where the flow of air through the device is less restricted.

In a further aspect, the method may also include administering respiratory treatment in response to a flow of air inhaled by a user. A nebulizer, a metered dose inhaler with a valved holding chamber, or a dry powder inhaler may administer the respiratory treatment in response to the flow of air inhaled by the user.

In another aspect, a respiratory treatment device includes a housing enclosing a chamber, an inlet configured to receive air into the chamber, an outlet configured to permit air to exit the chamber, and a vacuum in communication with the chamber, the vacuum being configured to generate a negative pressure in the chamber. A sealing member is moveable relative to the inlet and the outlet between a closed position where the flow of air through the inlet and the outlet is prevented, and an open position where the flow of air through the inlet and the outlet is permitted. The sealing member is biased toward the closed position by the negative pressure in the chamber. The sealing member is configured to move from the closed position to the open position when an exhalation pressure at the inlet is sufficient to overcome the bias on the sealing member by the negative pressure in the chamber.

In a further aspect, the sealing member may be rotatably mounted to the housing. The sealing member may be configured to rotate relative to the inlet and the outlet.

In a further aspect, a cross-sectional area of the outlet may be greater than a cross sectional area of the inlet.

In a further aspect, the sealing member may be biased by a spring toward the closed position.

In a further aspect, the device may include a mouthpiece in communication with the inlet. The device may also include a one-way inhalation valve positioned on the mouthpiece, the one-way inhalation valve being configured to open on inhalation, and close on exhalation.

In a further aspect, the vacuum may include an electric pump. Alternatively, the vacuum may include a manually operated pump.

In a further aspect, the device includes a pressure gauge in communication with the chamber.

In another aspect, a respiratory treatment device includes a housing enclosing a chamber, an inlet configured to receive air into the chamber, a first magnet positioned in proximity to the inlet, an outlet configured to permit air to exit the chamber, and, a second magnet positioned in proximity to the outlet. A shuttle is configured to move relative to the first magnet and the second magnet between a closed position where the flow of air through the inlet is blocked by the shuttle, and an open position where the flow of air through the outlet is blocked by the shuttle. The shuttle is configured to move from the closed position to the open position when an exhalation pressure at the at the inlet is sufficient to overcome a magnetic attraction force between the shuttle and the first magnet. The shuttle is configured to move from the open position to the closed position when an inhalation pressure in the chamber is sufficient to overcome a magnetic attraction force between the shuttle and the second magnet.

In a further aspect, the shuttle includes an insert subject to magnetic attraction.

In a further aspect, the first magnet may be positioned in the inlet. The second magnet may be positioned in the outlet.

In a further aspect, the device includes a mouthpiece in communication with the inlet. The device may also include a one-way inhalation valve configured to permit the flow of air through from the chamber into the mouthpiece.

In a further aspect, the device includes a one-way exhalation valve configured to permit the flow of air from the chamber out of the housing.

BRIEF DESCRIPTION OF THE DRAWINGS

FIGS. 29A-29B are perspective and cross-sectional views of an adjustment mechanism of the Huff Cough simulation device of FIG. 21;

FIG. 30 is a cross sectional side view of an alternative embodiment of the Huff Cough simulation device of FIG. 21, comprising a magnet and a screw;

FIG. 32 is an illustration of an eighth embodiment of a Huff Cough simulation device, showing the device unpressurized and in a closed position;

FIG. 33 is an illustration of the Huff Cough simulation device of FIG. 32, showing the device pressurized and in a closed position;

DETAILED DESCRIPTION

Figure 1:
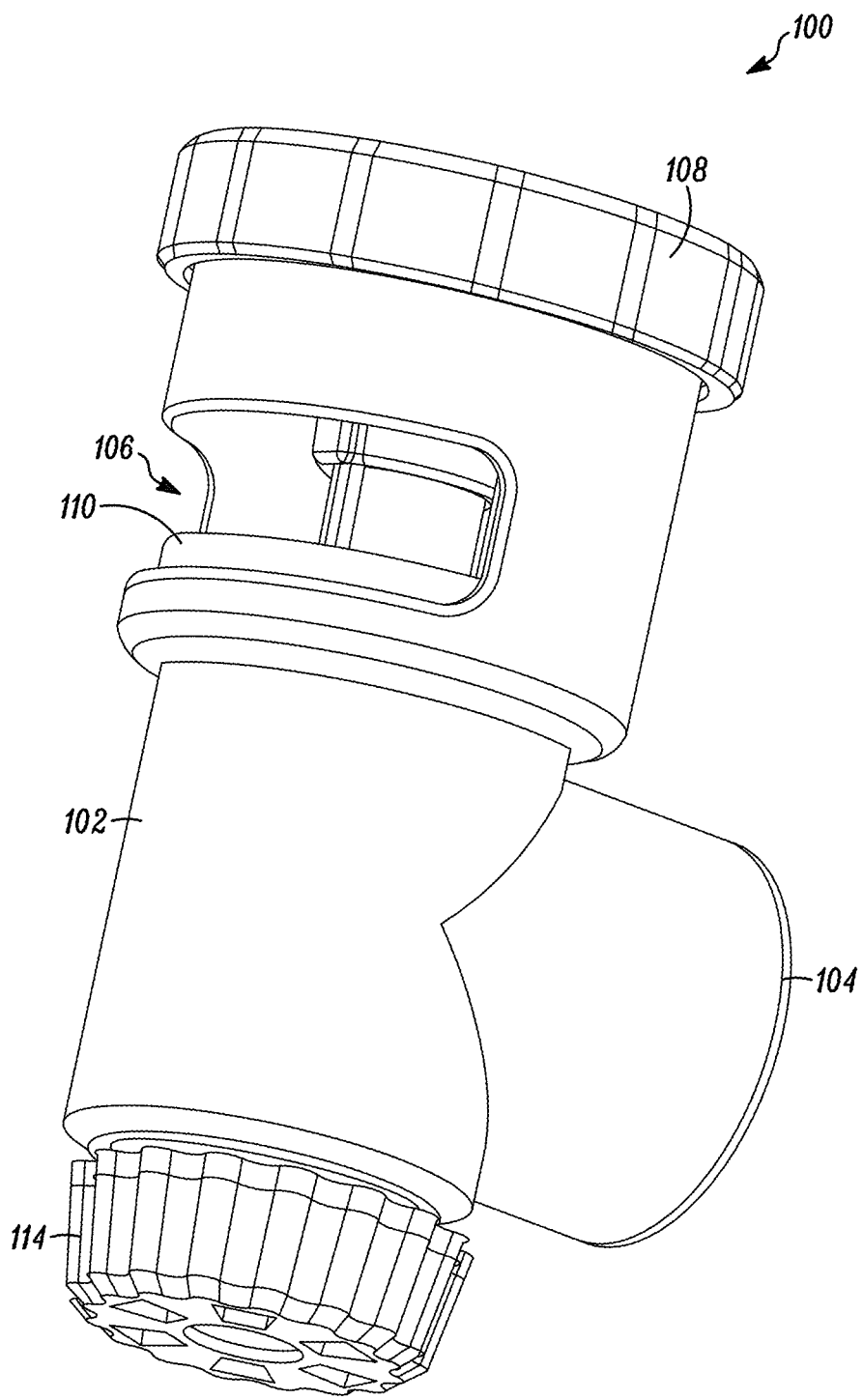
FIG. 1 is a perspective view of a first embodiment of a Huff Cough simulation device.

Described herein are embodiments of a respiratory treatment device that replicates or simulates a Huff Cough. In general, these embodiments prevent the flow of exhaled air through the device until a threshold pressure is reached at a user interface. Once a threshold pressure is reached, the device releases the exhaled air, causing a rapid increase in the flow of exhaled air through the device. This sharp increase in airflow translates directly to high air velocities in the user's airways, and therefore higher shear forces on secretions lining the airways, similar to that experienced during a Huff Cough.

The embodiments described herein are notable in that the threshold pressure at which exhaled air is released is selectively adjustable. These embodiments are also notable in that the release of exhaled at a threshold pressure is dependent on a user's exhalation and easily repeatable by a user without coaching or supervision from a respiratory professional.

First Embodiment

FIGS. 1-4 show a first embodiment of a Huff Cough simulation device 100. In general, the device 100 includes a housing 102 having an interior chamber 103; an inlet 104 and an outlet 106; a cap 108; a piston 110; a first pair of magnets 112a and 112b; a second pair of magnets 113a and 113b; and, an adjustment mechanism 114.

As show in FIGS. 1-4, the chamber inlet 104 may form a mouthpiece for receiving exhaled air from a user. Preferably, the inlet 104 or the mouthpiece is circular and roughly 1 inch in diameter in order to promote glottal patency throughout a user's exhalation. However, it should be appreciated that other user interfaces may form, or may be in fluid communication with the chamber inlet 104, including for example, gas masks, breathing tubes, or the like. Moreover, it should be appreciated that the device 100 may be used in conjunction or combination with other respiratory treatment devices that administer therapy upon inhalation, including for example, a nebulizer, a metered dose inhaler with a valved holding chamber, or a dry powder inhaler. In this way, the Huff Cough simulation device 100 may administer therapy upon a user's exhalation, while the aforementioned devices may administer therapy upon a user's inhalation.

At one end of the device 100, the cap 108 may be removably secured to the housing 102 by threading, such that the interior chamber 103 and the components contained therein may be periodically accessed for cleaning, modification, and/or replacement. The cap 108 includes a cylindrical opening or slot 116 configured to receive a shaft portion 118 of the piston 110. The cylindrical opening or slot 116 and the shaft portion 118 may be keyed to prevent rotation of the piston 110 and limit the piston 110 to linear movement within the interior chamber 103 of the housing 102.

Figure 3:
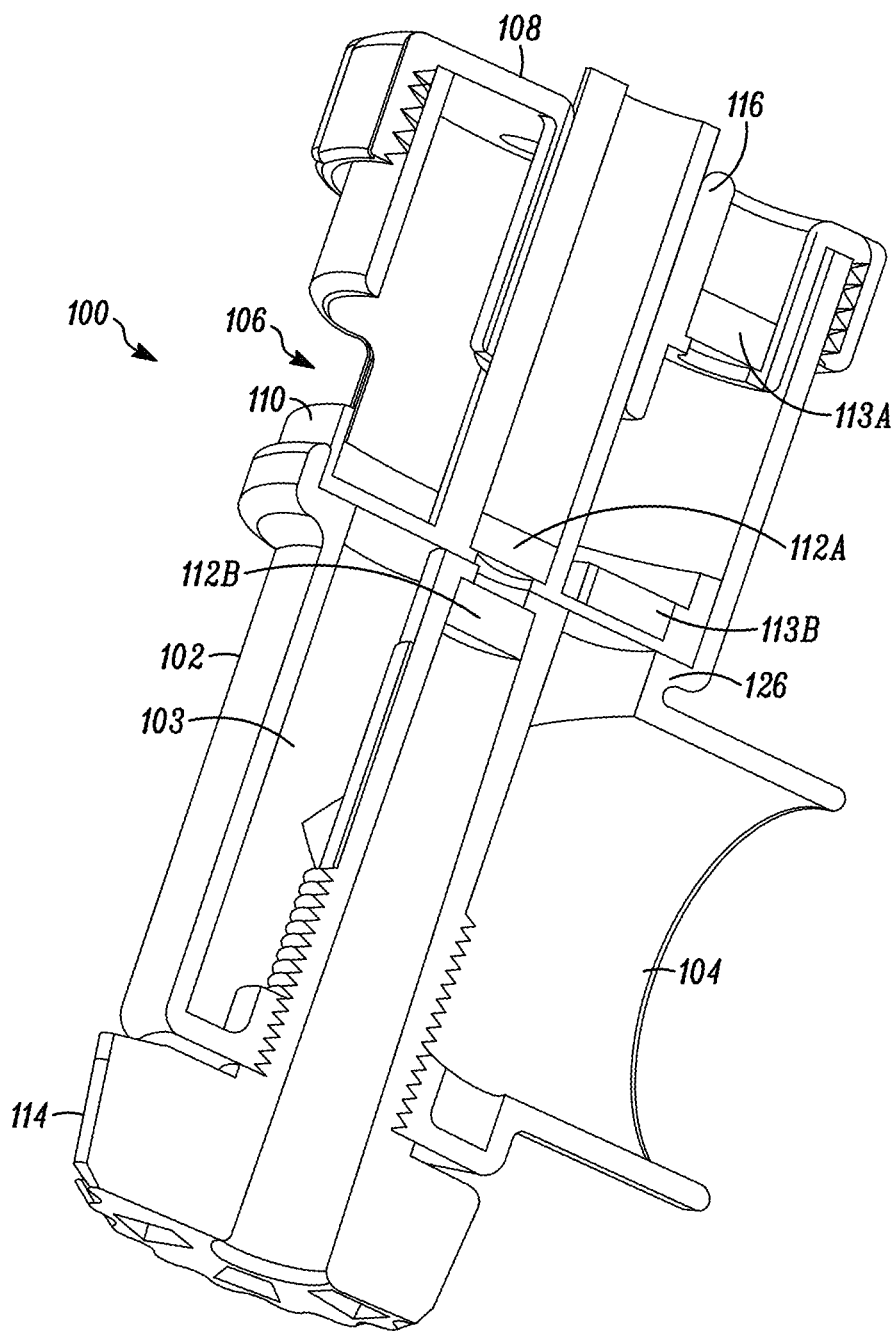
FIG. 3 is a cross-sectional perspective view of the Huff Cough simulation device of FIG. 1, showing the device in a closed position.
Figure 4:
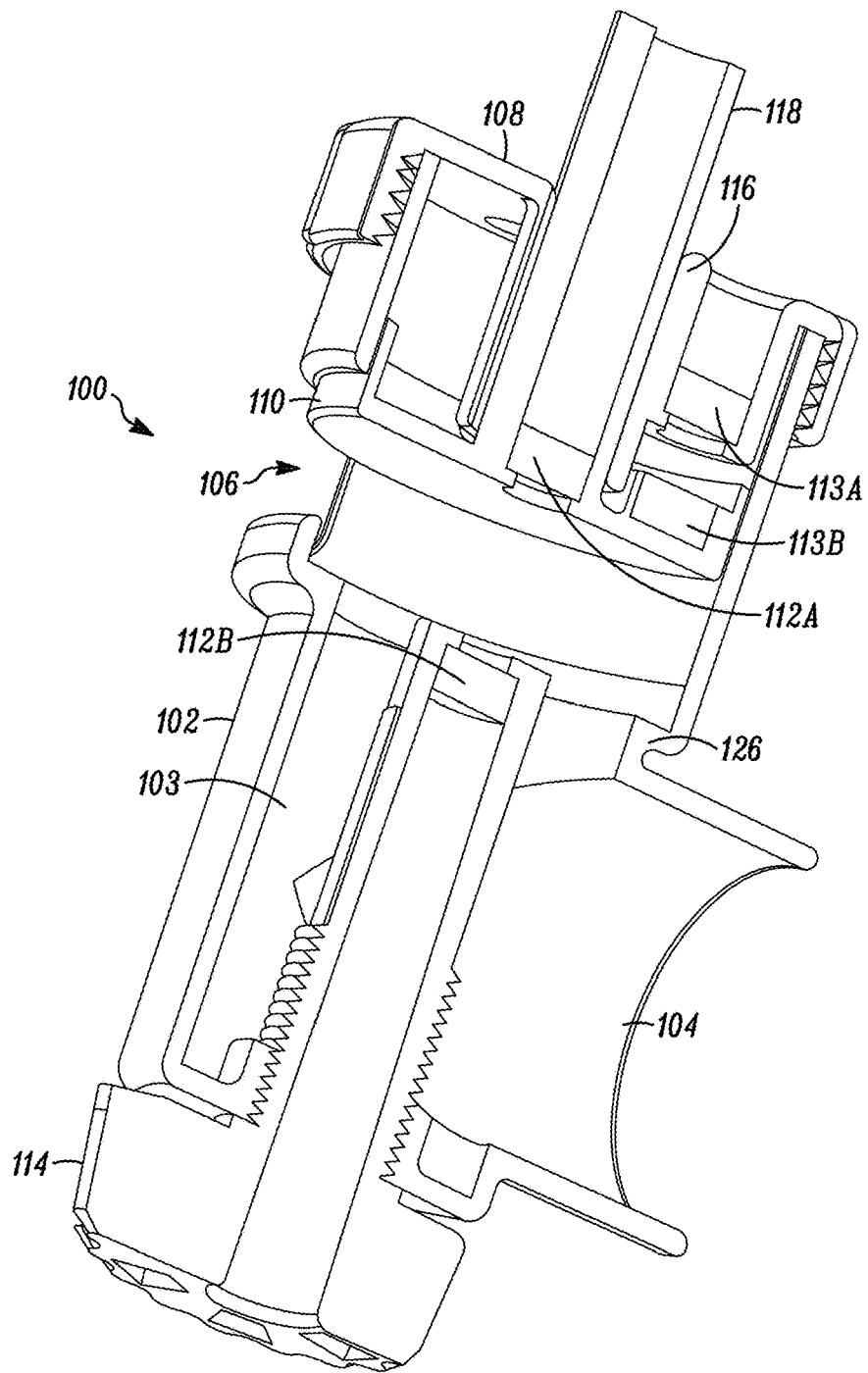
FIG. 4 is a cross-sectional perspective view of the Huff Cough simulation device of FIG. 1, showing the device in an open position.
Figure 5:
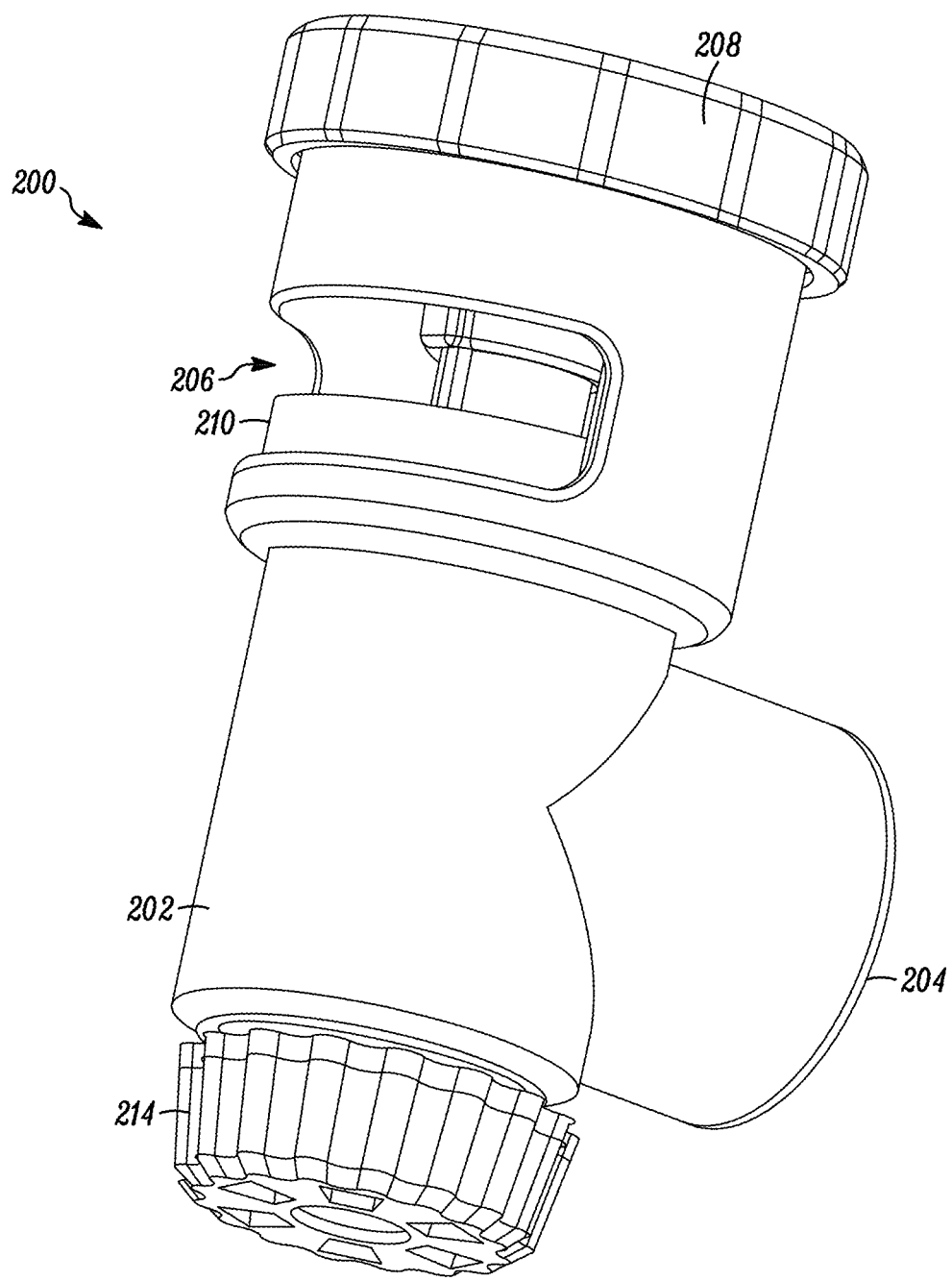
FIG. 5 is a perspective view of a second embodiment of a Huff Cough simulation device.
Figure 6:
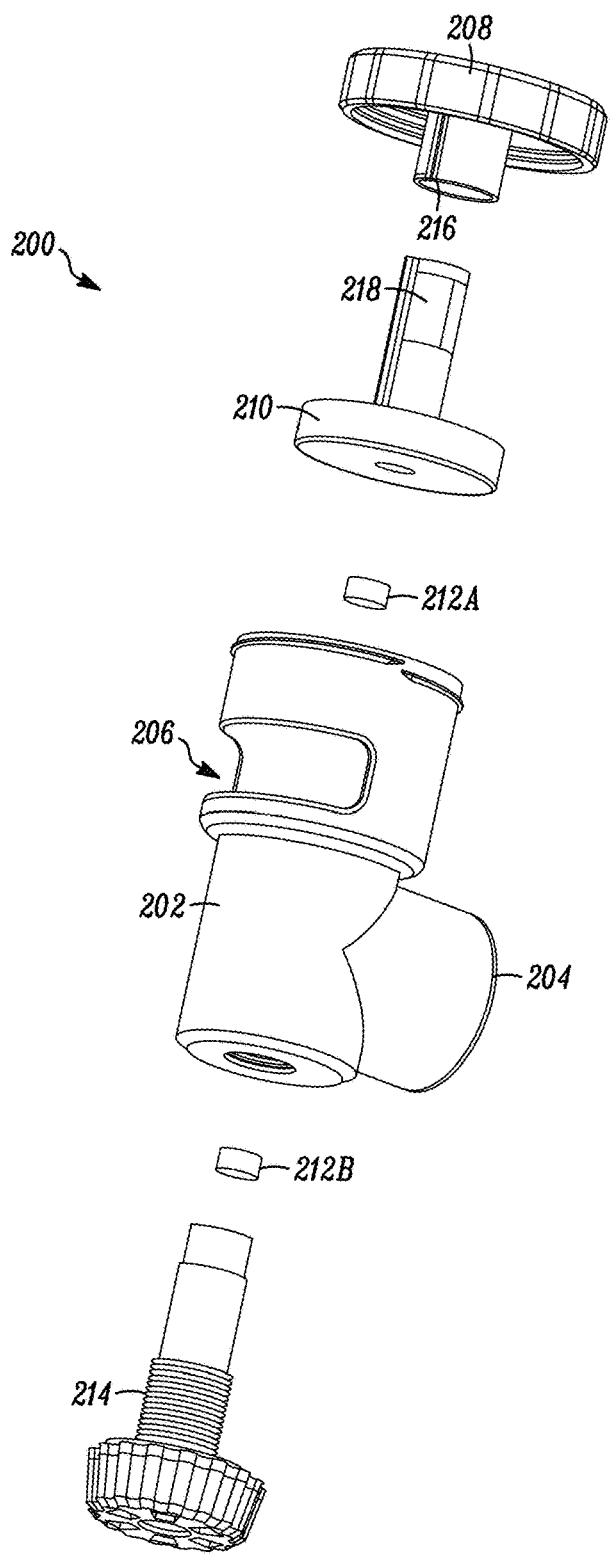
FIG. 6 is an exploded view of the Huff Cough simulation device of FIG. 5.

As described herein, the piston is configured to move between a closed position, as seen in FIG. 3, where exhaled air is blocked by the piston 110 from flowing through the device 100 between the inlet 104 and the outlet 106, and an open position, as seen in FIG. 4, where exhaled air is free to flow through the device 100 between the inlet 104 and the outlet 106. Movement of the piston 110 in one direction may be limited by a ledge 126 formed within the housing 102 that is configured to engage and prevent the flow of exhaled air past the piston 110.

Figure 2:
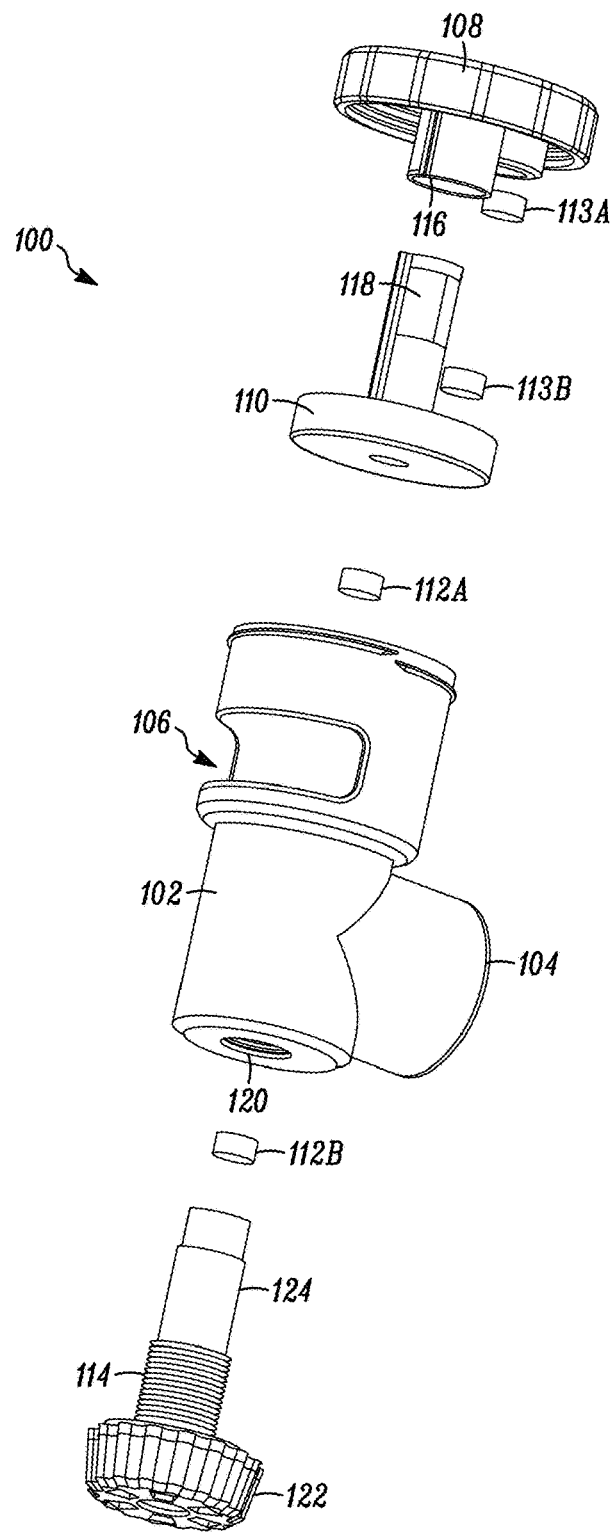
FIG. 2 is an exploded view of the Huff Cough simulation device of FIG. 1.

At the other end of the device 100, the adjustment mechanism 114 is inserted in to a cylindrical opening 120. As best seen in FIG. 2, the adjustment mechanism 114 includes a knob 122 and a shaft 124 that extends into the interior chamber 103 of the housing 102. A portion of the shaft 124 on the adjustment mechanism 114 and the opening 120 may be threaded, such that the knob 122 may be selectively rotated relative to the housing 102 to thereby advance or retract the shaft 124 of the adjustment mechanism 114 within the interior chamber 103 of the housing 102.

The device 100 also includes a first pair of magnets 112a and 112b. One magnet 112a of the first pair of magnets is positioned on or within the piston 110, while the other magnet 112b is positioned on or within an end of the shaft 124 of the adjustment mechanism 114 within the interior chamber 103 of the housing 102. The pair of magnets 112a and 112b are configured such that their polarities cause the pair of magnets 112a and 112b to be attracted to one another, thereby biasing the piston 110 toward the adjustment mechanism 114 when the piston 110 is in proximity to the adjustment mechanism 114, such as for example, when the piston 110 is in a closed position. Because the magnetic attraction force between the magnets 112a and 112b is inversely proportional to the distance between the magnets 112a and 112b (i.e., $F \propto 1/r^3$), an increase in the distance between the magnets 112a and 112b will result in a rapid decrease in biasing force acting on the piston 110, while a decrease in the distance between the magnets 112a and 112b will result in a rapid increase in the biasing force acting on the piston 110. The size and strength of the magnets 112a and 112b may be selected and/or replaced as necessary to achieve the desired biasing force acting on the piston 110 when the piston 110 is in a closed position, and therefore, the desired threshold pressure required to move the piston 110 from a closed position to an open position.

The device 100 further includes a second pair of magnets 113a and 113b. One magnet 113a of the second pair of magnets is positioned on or within the cap 108, while the other magnet 113b is positioned on or within the piston 110. The pair of magnets 113a and 113b are configured such that their polarities cause the pair of magnets 113a and 113b to be attracted to one another, thereby biasing the piston 110 toward the cap 108 when the piston 110 is in proximity to the cap 108, such as for example, when the piston 110 is in an open position. The size and strength of the magnets 113a and 113b may be selected and/or replaced as necessary to provide a biasing force sufficient to retain the piston 110 in an open position.

Operation of the Huff Cough simulation device 100 will now be described. Administration of treatment using the device 100 begins with the piston 100 in a closed position, for example, as shown in FIG. 3. In this position, the flow of exhaled air through the device 100 between the inlet 104 and the outlet 106 is blocked by the piston 110. In this position, the first pair of magnets 112a and 112b are in proximity to one another, such that the piston 110 is biased toward the adjustment mechanism 114, or toward a closed position. As a user exhales into the inlet 104, pressure within the interior chamber 103 of the housing 102 begins to build, and the force acting on the piston 110 resulting from such pressure increases (i.e., $F=P \times A$). When a threshold pressure is reached, the force acting on the piston 110 resulting from the increased pressure in the interior chamber 103 of the housing 102 surpasses the biasing force acting on the piston 110 as a result of the magnetic attraction between the first pair of magnets 112a and 112b, causing the piston 110 to lift off the ledge 126. As extra surface area of the piston 110 becomes exposed to the increased pressure within the interior chamber 103 of the housing 102, the force acting on the piston 110 increases proportional to the increased surface area of the piston 110. Coupled with the rapid decay in magnetic attraction force due to the increase in distance between the magnets 112a and 112b, the piston 110 moves rapidly from a closed position to an open position, for example, as shown in FIG. 4. As the piston 110 moves from a closed position to an open position, the exhaled air in the interior chamber 103 of the housing 102 and air in a user's airways is free to move through the device 100 between the inlet 104 and the outlet 106. This sudden release of built up pressure in the device 100 and in the user's airways translates to high velocity airflow through the user's airways that simulates a Huff Cough.

As the piston 110 moves to an open position, shown in FIG. 4, the second pair of magnets 113a and 113b are moved in to proximity, thereby biasing the piston 110 toward the cap 108. With the magnets 113a and 113b in proximity to one another, the magnetic attraction force between the magnets 113a and 113b is sufficient to retain the piston 110 in an open position. In this position, the shaft portion 118 of the piston 110 extends outside of the housing 102 beyond the cap 108, such that a user may push the shaft portion 118 of the piston 110 back into the housing 102, returning the piston 110 to a closed position. As the piston is returned to a closed position, the first pair of magnets 112a and 112b is moved in to proximity with one another, such that the piston 110 is biased toward the adjustment mechanism 114 and in engagement with the ledge 126. The user may then repeat the above cycle.

Second Embodiment

FIGS. 5-8 show a second embodiment of a Huff Cough simulation device 200. In general, like the Huff Cough simulation device 100, the device 200 includes a housing 202 having an interior chamber 203; an inlet 204 and an outlet 206; a cap 208; a piston 210; a pair of magnets 212a and 212b; and, an adjustment mechanism 214. Except for as described below, the structure and operation of the device 200 is otherwise the same as described above with regards to the device 100.

The device 200 does not include a second pair of magnets to bias the piston 210 toward the cap 208 when the piston 210 is in proximity to the cap 208. Rather, the cylindrical opening or slot 216 on the cap 208 includes a catch or a groove 228, while the piston 210 includes a ridge or protrusion 230, the combination of which operate as a mechanical latch that can retain the piston 210 in the position shown in FIG. 8.

Figure 7:
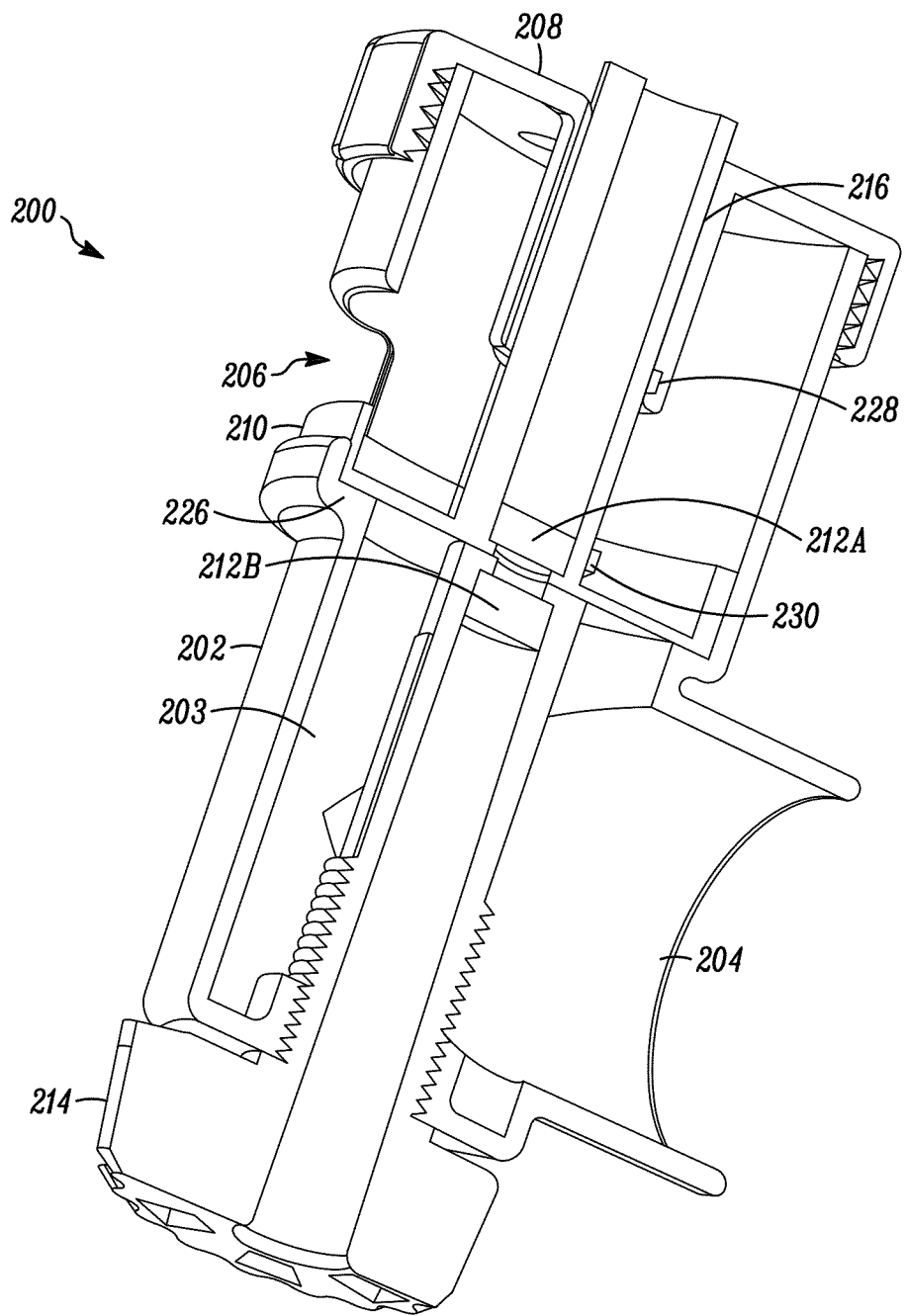
FIG. 7 is a cross-sectional perspective view of the Huff Cough simulation device of FIG. 5, showing the device in a closed position.
Figure 8:
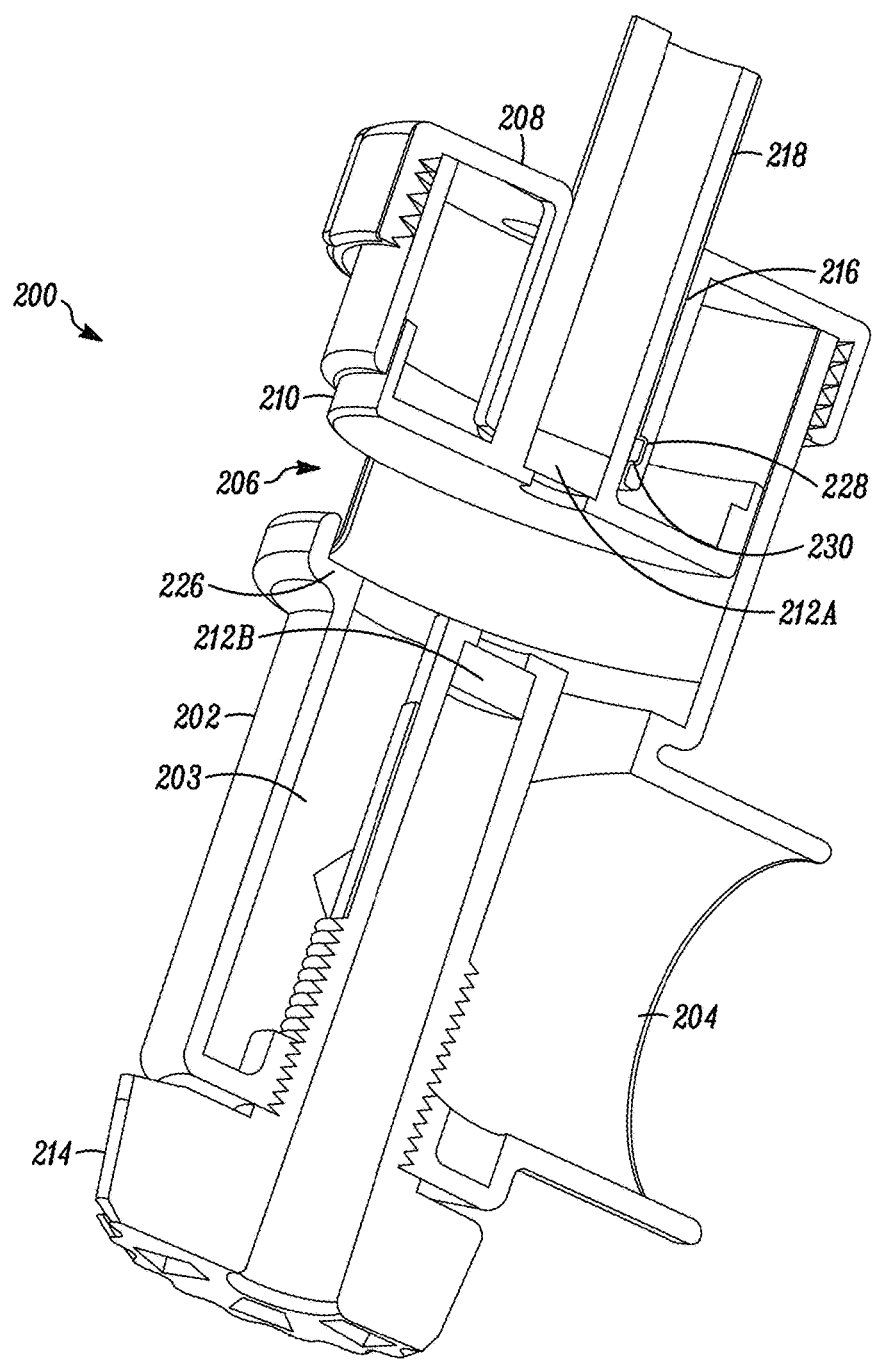
FIG. 8 is a cross-sectional perspective view of the Huff Cough simulation device of FIG. 5, showing the device in an open position.
Figure 9:
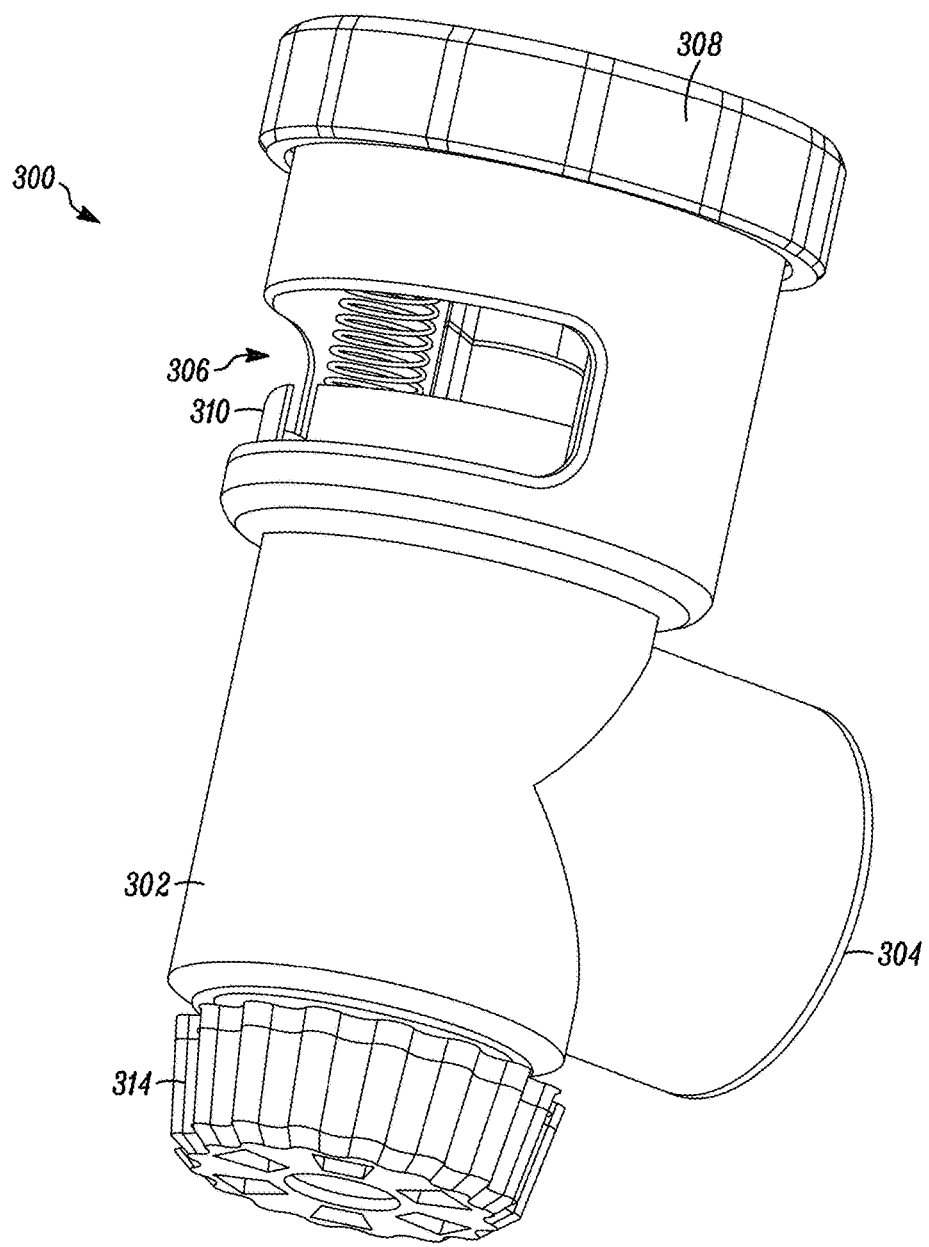
FIG. 9 is a perspective view of a third embodiment of a Huff Cough simulation device.
Figure 10:
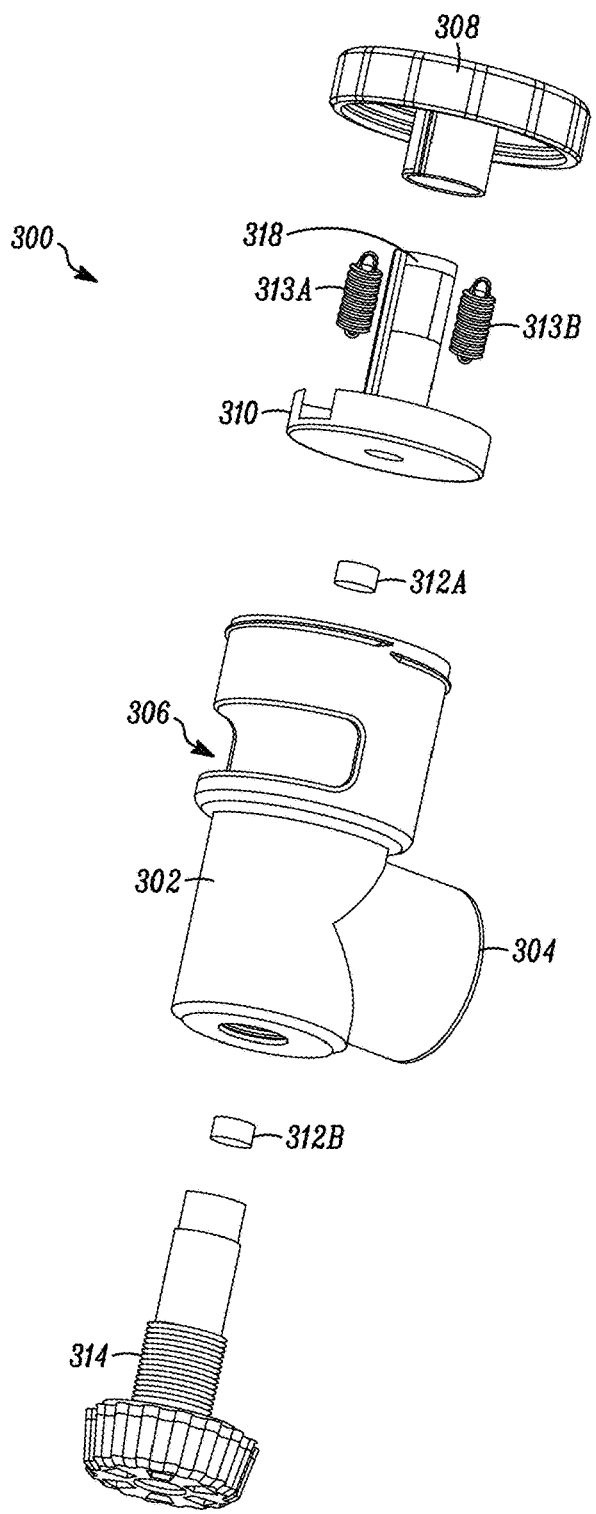
FIG. 10 is an exploded view of the Huff Cough simulation device of FIG. 9.

When the device 200 is used as described above with regards to the device 100, and a threshold pressure is reached in the interior chamber 203 of the housing 202, the piston 210 is rapidly driven from a closed position, as shown in FIG. 7, to an open position, as shown in FIG. 8. As the piston 210 moves to an open position shown in FIG. 8, the ridge or protrusion 230 on the piston 210 engages the catch or groove 228 on the cylindrical opening or slot 216 of the cap 208, such that the piston 210 is retained in an open position shown in FIG. 8. In this position, the shaft portion 218 of the piston 210 extends outside of the housing 202 beyond the cap 208, such that a user may push the shaft portion 218 of the piston 210 back into the housing 202, returning the piston 210 to a closed position. As the piston is returned to a closed position, the pair of magnets 212a and 212b is moved in to proximity with one another, such that the piston 210 is biased toward the adjustment mechanism 214 and in engagement with the ledge 226. The user may then repeat the above cycle.

Third Embodiment

FIGS. 9-12 show a third embodiment of a Huff Cough simulation device 300. In general, like the Huff Cough simulation device 100, the device 300 includes a housing 302 having an interior chamber 303; an inlet 304 and an outlet 306; a cap 308; a piston 310; a pair of magnets 312a and 312b; and, an adjustment mechanism 314. Except for as described below, the structure and operation of the device 300 is otherwise the same as described above with regards to the device 100.

Figure 11:
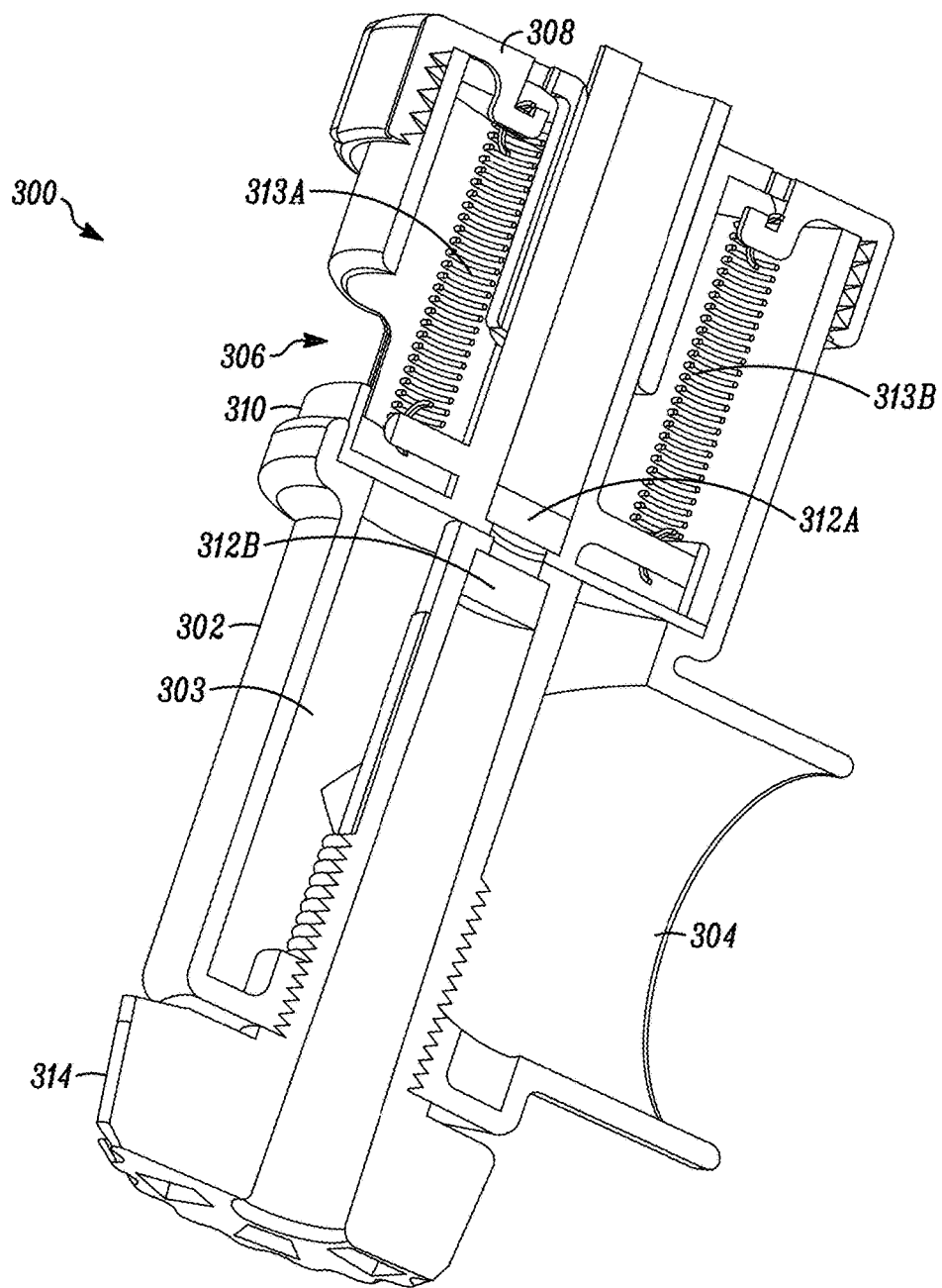
FIG. 11 is a cross-sectional perspective view of the Huff Cough simulation device of FIG. 9, showing the device in a closed position.
Figure 12:
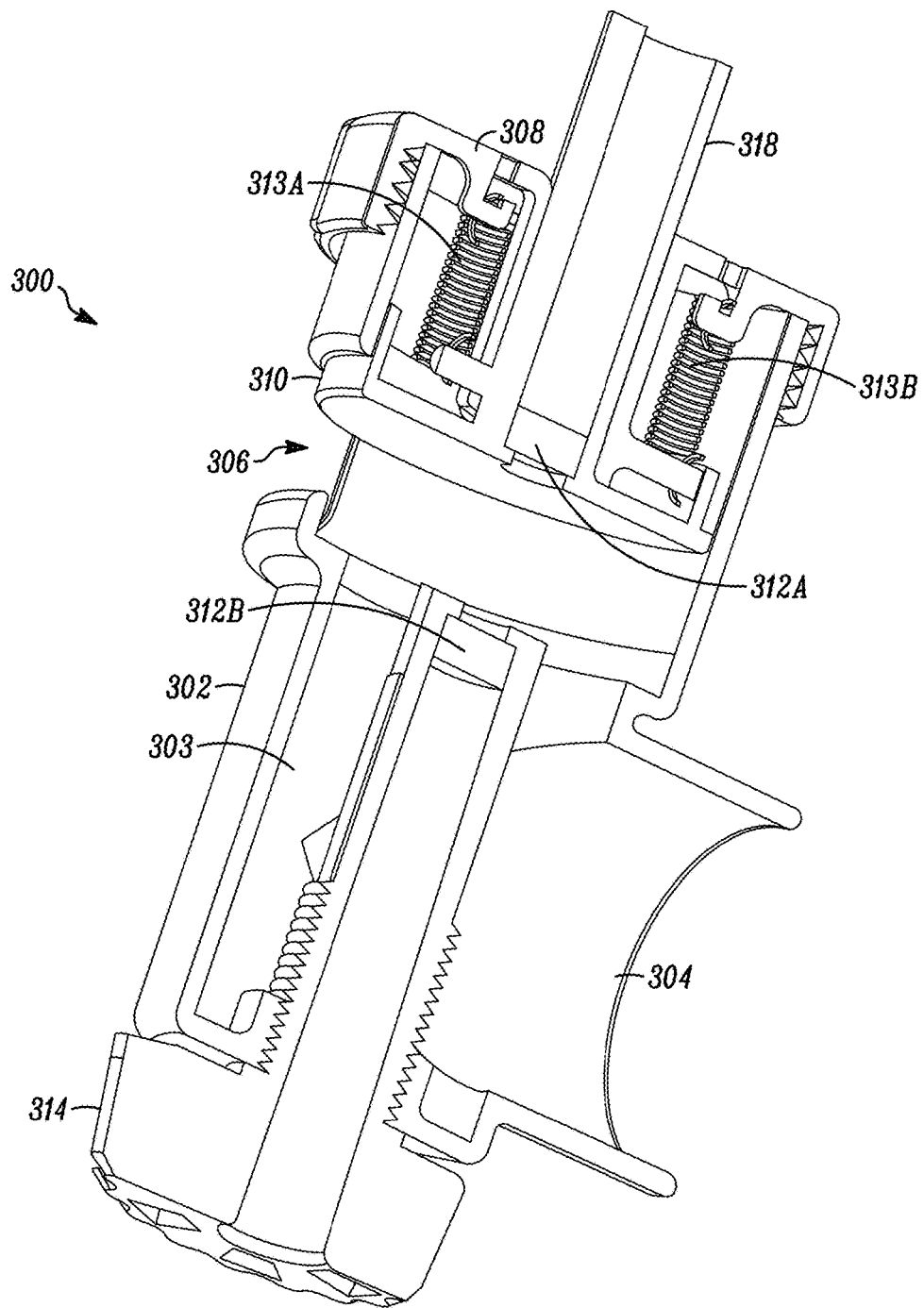
FIG. 12 is a cross-sectional perspective view of the Huff Cough simulation device of FIG. 9, showing the device in a open position.

Like the device 200, the device 300 does not include a second pair of magnets to bias the piston 310 toward the cap 308 when the piston 310 is in proximity to the cap 308. Rather, the device 300 has a pair of springs 313a and 313b, connecting the cap 308 and the piston 310, that operate to retain the piston 310 in the position shown in FIG. 12. The pair of springs 313a and 313b are configured such that the springs 313a and 313b are under tension when the piston 310 is in a closed position, as shown in FIG. 11. In this position, however, the tension in the pair of springs 313a and 313b is not sufficient to overcome the biasing force on the piston 310 toward the adjustment mechanism 314 provided by the magnetic attraction between the pair of magnets 312a and 312b, such that the piston 310 moves from a closed position to an open position. The size, length, and stiffness of the springs 312a and 312b may be selected and/or replaced as necessary to provide a biasing force sufficient to retain the piston 310 in an open position When the device 300 is used as described above with regards to the device 100, and a threshold pressure is reached in the interior chamber 303 of the housing 302, the piston 310 is rapidly driven from a closed position, as shown in FIG. 11, to an open position, as shown in FIG. 12. Once the piston 310 moves to an open position shown in FIG. 12, the tension in the pair of springs 313a and 313b operate to retain the piston 310 in the position sown in FIG. 12. In this position, the shaft portion 318 of the piston 310 extends outside of the housing 302 beyond the cap 308, such that a user may push the shaft portion 318 of the piston 310 back into the housing 302, returning the piston 310 to a closed position. As the piston is returned to a closed position, the pair of magnets 312a and 312b are moved in to proximity with one another, such that the piston 310 is biased toward the adjustment mechanism 314 and in engagement with the ledge 326. The user may then repeat the above cycle.

Fourth Embodiment

FIGS. 13-16 show a fourth embodiment of a Huff Cough simulation device 400. In general, the device 400 includes a housing 402 having an interior chamber 403; an inlet 404 and an outlet 406; a cap 408; a piston 410 having a shaft portion 418; a cylinder 411; a spring 412; and, an adjustment mechanism 414.

At one end of the device 400, the cylinder 411 extends from the housing 402, and is shaped and sized to accommodate the piston 410 and the spring 412. A stop 426 may be formed at the intersection of the cylinder 411 and the housing 402 to limit the movement of the piston 410 within the cylinder 411. The stop may also include a slot 416 configured to receive the shaft portion 418 of the piston 410 that extends beyond the cylinder 411 into the interior chamber 403 of the housing 402. A guide rail 433 may also be provided within the interior chamber 403 of the housing 402 adapted to guide reciprocal movement of the shaft portion 402 of the piston 410 along a linear path.

At the end of the cylinder 411 opposite the stop 426, the adjustment mechanism 414 may be attached to the cylinder 411 by threading, effectively retaining the spring 412 and the piston 410 within the cylinder 411. The size, length, and stiffness of the spring 412 may be selected and/or replaced as necessary such that, when retained in the cylinder 411, the spring 412 is under compression, thereby biasing the piston 410 toward the position shown in FIG. 15. The adjustment mechanism 414 may also be rotated relative to the housing 412, and therefore the cylinder 411, thereby retracting or advancing the position of the adjustment mechanism 411 relative to the ledge or stop 426. In this way, a user may selectively adjust the amount of compression in the spring 412 and bias on the piston 410, and therefore, the threshold pressure required to open the cap 408.

Figure 13:
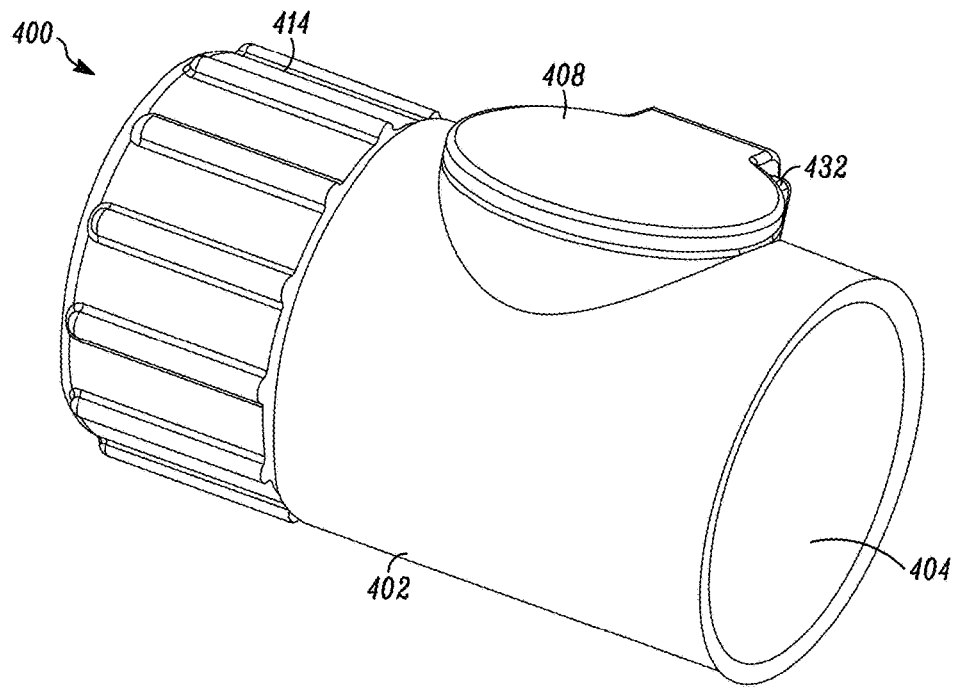
FIG. 13 is a perspective view of a fourth embodiment of a Huff Cough simulation device.
Figure 14:
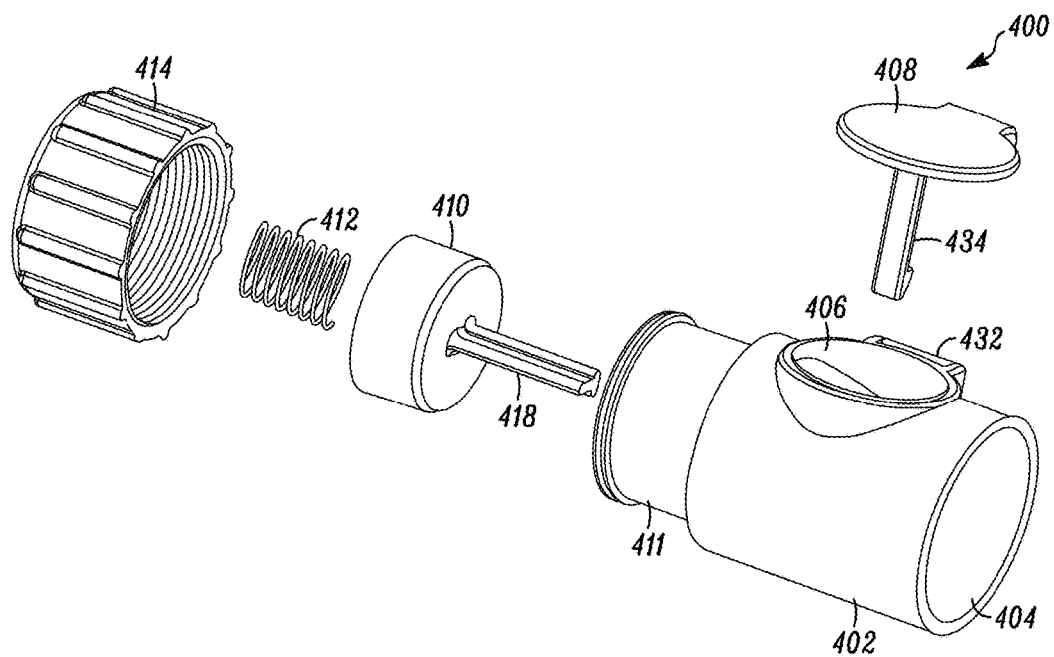
FIG. 14 is an exploded view of the Huff Cough simulation device of FIG. 13.
Figure 15:
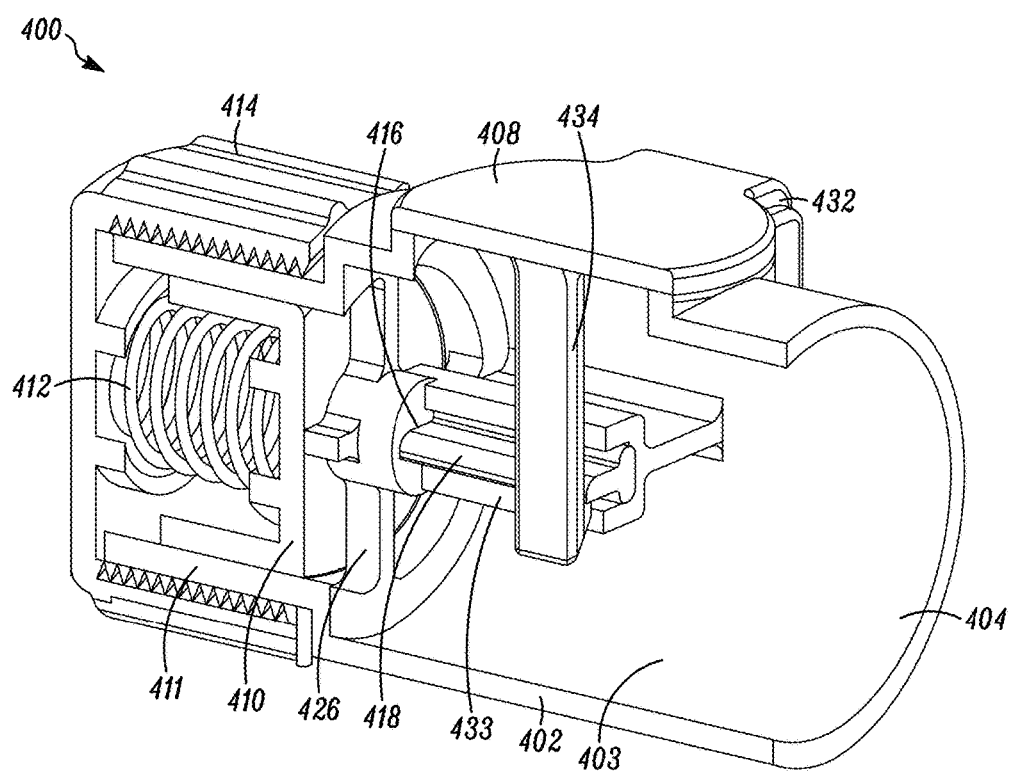
FIG. 15 is a cross-sectional perspective view of the Huff Cough simulation device of FIG. 13, showing the device in a closed position.
Figure 16:
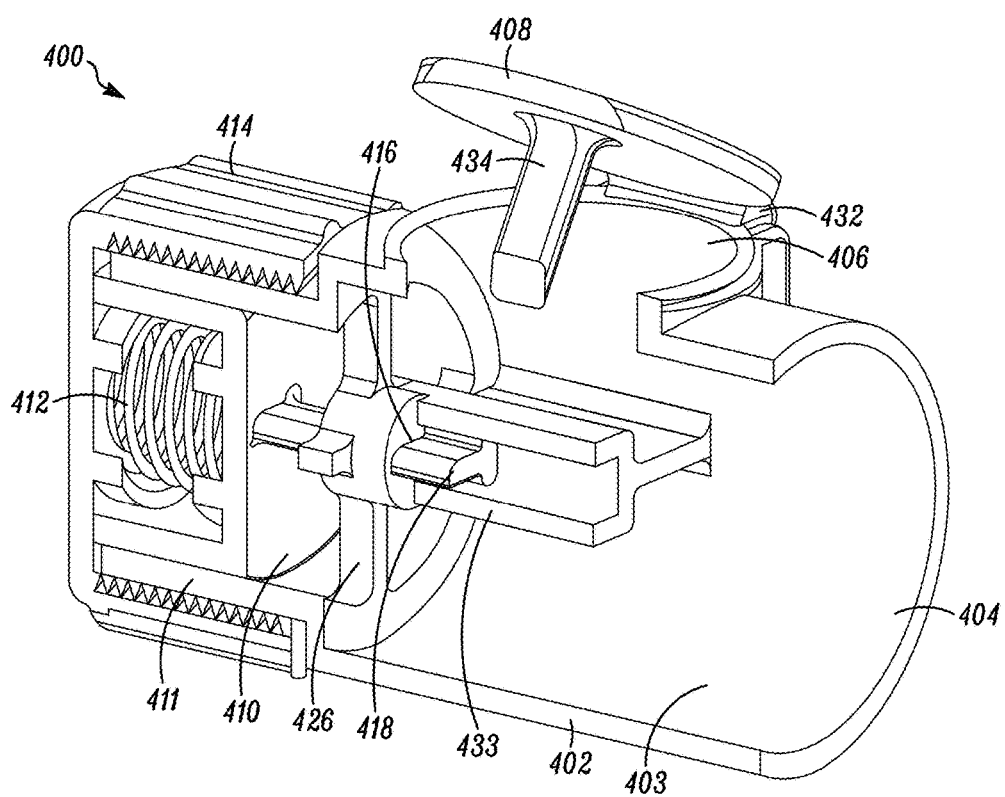
FIG. 16 is a cross-sectional perspective view of the Huff Cough simulation device of FIG. 13, showing the device in an open position.

The cap 408 is positioned and sized to cover the outlet 406, and may be rotatably attached to the housing 402, for example by a hinge 432, such that the cap is moveable between a closed position, as shown in FIGS. 13 and 15, and an open position, as shown in FIG. 16. Extending from the cap 408 into the interior chamber 403 of the housing 402 is a latch 434 adapted to engage the shaft portion 418 of the piston 410 and bias or retain the cap 408 in a closed position, as shown in FIG. 15.

Operation of the Huff Cough simulation device 400 will now be described. Administration of treatment using the device 400 begins with the cap 408 in a closed position, for example, as shown in FIGS. 13 and 15. In this position, the flow of exhaled air through the device 400 between the inlet 404 and the outlet 406 is blocked by the cap 408. In this position, the cap 408 is biased or retained in a closed position by the latch 434 engaged with the shaft portion 418 of the piston 410. Prior to a user exhaling into the inlet 404, the piston 410 is biased by the spring 412 such that it is engaged with the stop 426, as shown in FIG. 15.

As a user exhales into the inlet 404, pressure within the interior chamber 403 of the housing 402 begins to build, and the force acting on the piston 410 resulting from such pressure increases. As the force acting on the piston 410 increases, the spring 412 is compressed, allowing the piston 410 to move in a direction toward the adjustment mechanism 414. As the piston 410 moves toward the adjustment mechanism 414, the shaft portion 418 of the piston 410 slides along the guide rail 433, from the position shown in FIG. 15, toward the position shown in FIG. 16. When the end of the shaft portion 418 of the piston 410 slides past the latch 434 extending from the cap 408 into the interior chamber 403 of the housing 402, the cap 408 is no longer biased or retained in a closed position, thus allowing the cap 408 to burst open as a result of the force acting on the cap 408 from the increased pressure in the interior chamber 403 of the housing 402. In an open position, shown in FIG. 16, the exhaled air in the interior chamber 403 of the housing 402 and air in a user's airways is free to move through the device 400 between the inlet 404 and the outlet 406. This sudden release of built up pressure in the device 400 and in the user's airways translates to high velocity airflow through the user's airways that simulates a Huff Cough.

As the pressure in the device 400 is released, the force acting on the piston 410 decreases, causing the biasing force from the spring 412 on the piston 410 to return the piston 410 to the position shown in FIG. 15. In this position, a user may press and rotate the cap to a closed position, as shown in FIG. 15, returning the latch 434 to engagement with the shaft portion 418 of the piston 410. The user may then repeat the above cycle.

Fifth Embodiment

FIGS. 17-20 show a fifth embodiment of a Huff Cough simulation device 500. In general, the device 500 includes a housing 502 having an interior chamber 503; an inlet 504 and an outlet 506; a cap 508; a pair of magnets 512a and 512b; and, an adjustment mechanism 514.

Figure 17:
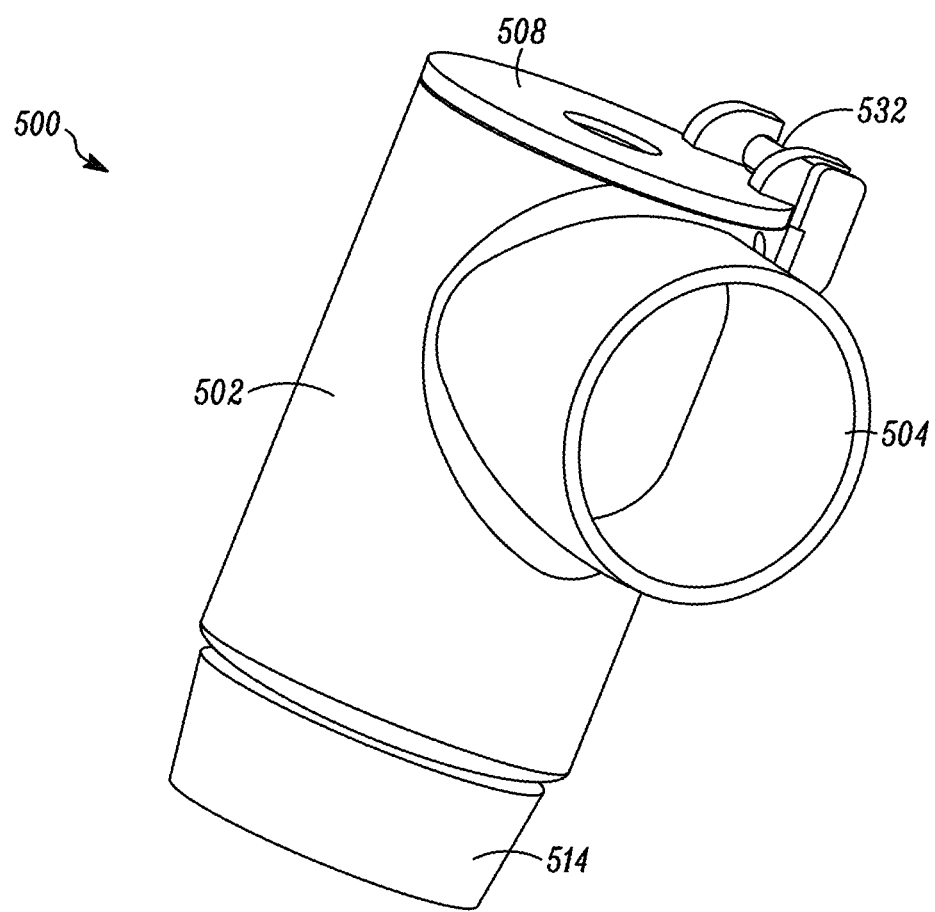
FIG. 17 is a perspective view of a fifth embodiment of a Huff Cough simulation device.
Figure 19:
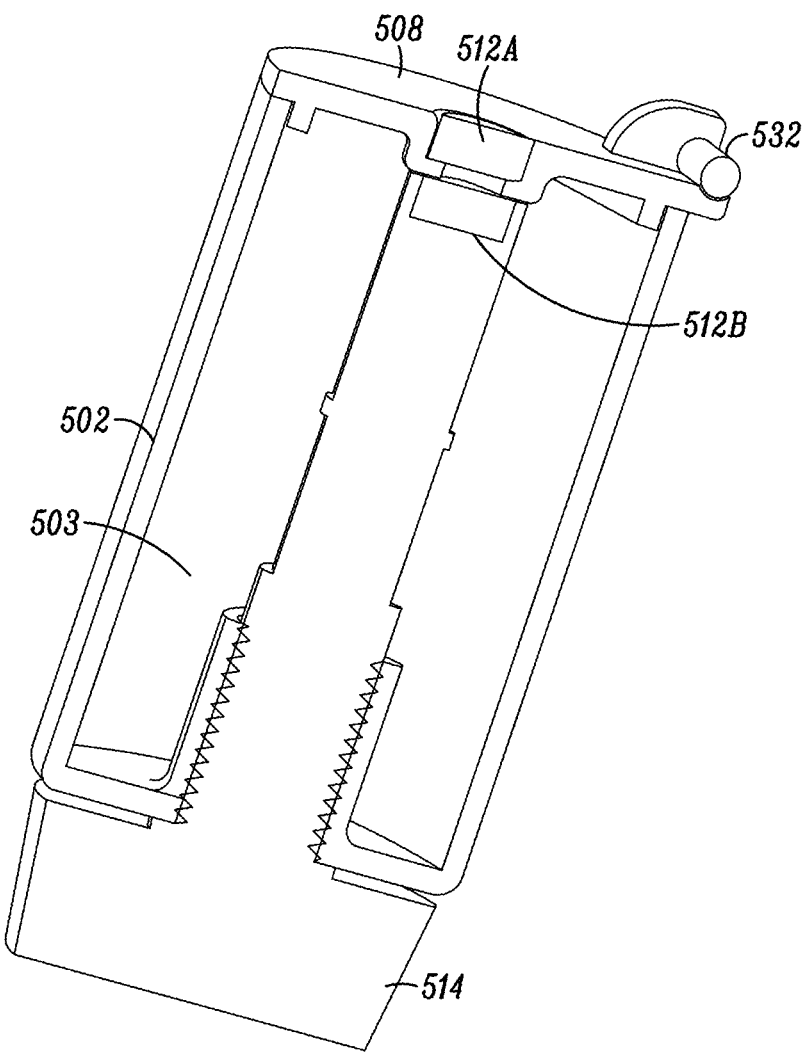
FIG. 19 is a cross-sectional perspective view of the Huff Cough simulation device of FIG. 17, showing the device in a closed position.
Figure 20:
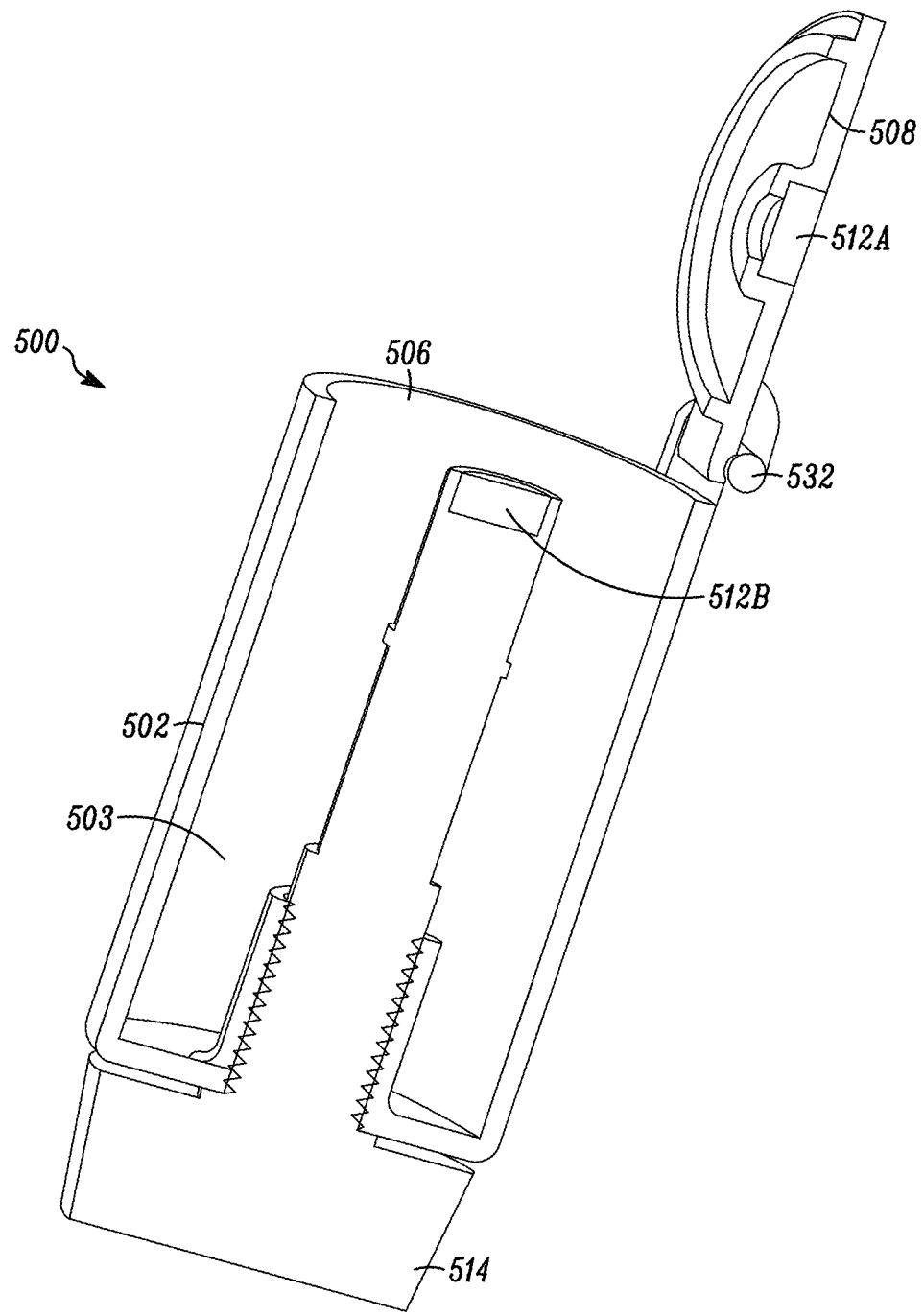
FIG. 20 is a cross-sectional perspective view of the Huff Cough simulation device of FIG. 17, showing the device in an open position.

At one end of the device 500, the cap 508 is positioned and sized to cover the outlet 506, and may be rotatably attached to the housing 502, for example by a hinge 532, such that the cap is moveable between a closed position, as shown in FIGS. 17 and 19, and an open position, as shown in FIG. 20.

Figure 18:
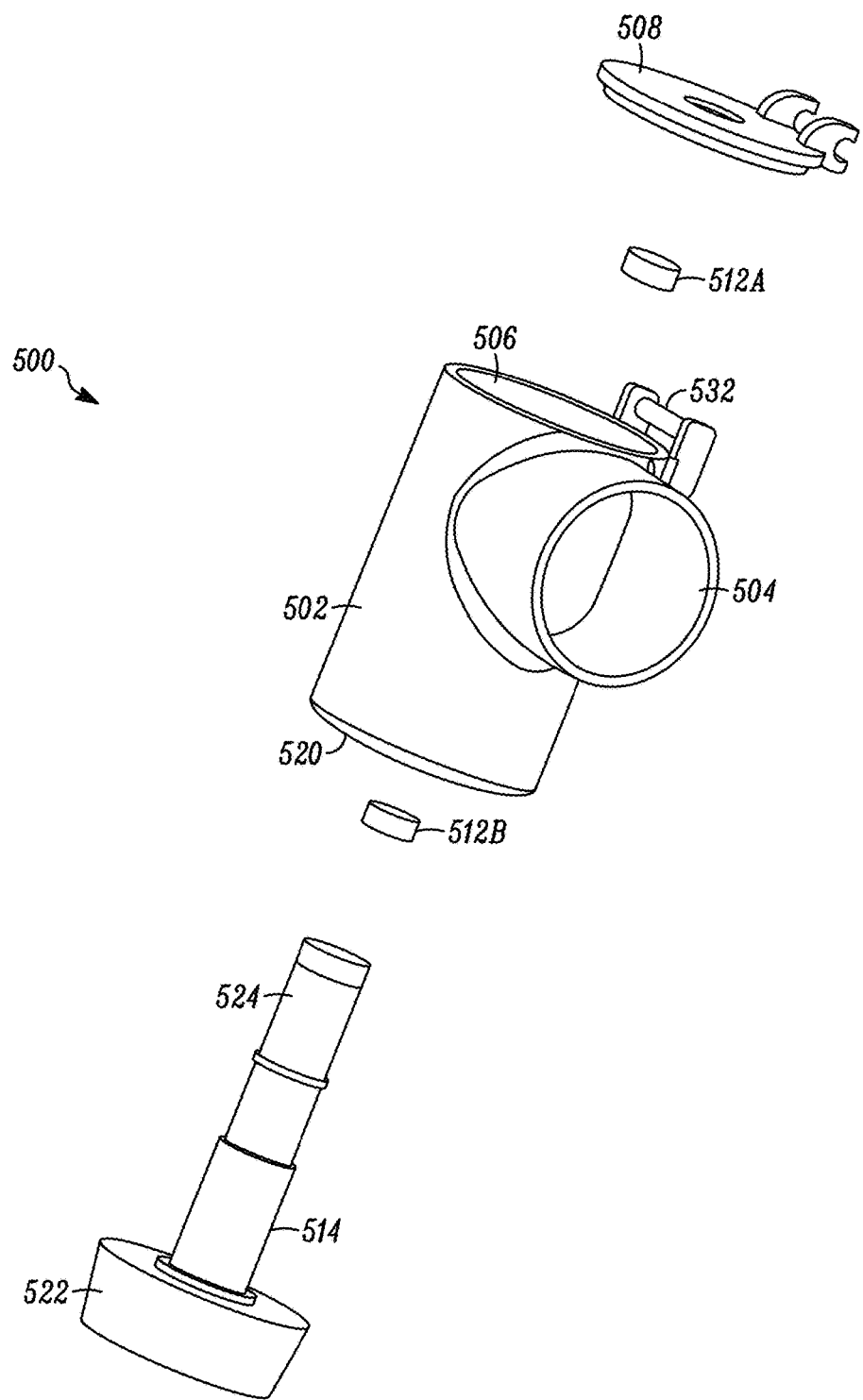
FIG. 18 is an exploded view of the Huff Cough simulation device of FIG. 17.

At the other end of the device 500, the adjustment mechanism 514 is inserted in to a cylindrical opening 520. As best seen in FIG. 18, the adjustment mechanism 514 includes a knob 522 and a shaft 524 that extends into the interior chamber 503 of the housing 502. A portion of the shaft 524 on the adjustment mechanism 514 and the opening 520 may be threaded, such that the knob 522 may be selectively rotated relative to the housing 502 to thereby advance or retract the shaft 524 of the adjustment mechanism 514 within the interior chamber 503 of the housing 502.

The device 500 also includes a pair of magnets 512a and 512b. One magnet 512a of the pair of magnets is positioned on the cap 508, while the other magnet 512b is positioned on an end of the shaft 524 of the adjustment mechanism 514 within the interior chamber 503 of the housing 502. The pair of magnets 512a and 512b are configured such that their polarities cause the pair of magnets 512a and 512b to be attracted to one another, thereby biasing the cap 508 toward the adjustment mechanism 514 when the cap 508 is in proximity to the adjustment mechanism 514, for example, when the cap 508 is in a closed position.

Because the magnetic attraction force between the magnets 512a and 512b is proportional to the distance between the magnets 512a and 512b (i.e., $F \propto 1/r^3$), an increase in the distance between the magnets 512a and 512b will result in a decrease in biasing force acting on the cap 508, while a decrease in the distance between the magnets 512a and 512b will result in an increase in the biasing force acting on the cap 508. The size and strength of the magnets 512a and 512b may be selected and/or replaced as necessary to achieve the desired biasing force acting on the cap 508, and therefore, the threshold pressure required to move the cap 508 from a closed position to an open position.

Operation of the Huff Cough simulation device 500 will now be described. Administration of treatment using the device 500 begins with the cap 508 in a closed position, as shown in FIGS. 17 and 19. In this position, the flow of exhaled air through the device 500 between the inlet 504 and the outlet 506 is blocked by the cap 508. In this position, the pair of magnets 512a and 512b are in proximity to one another, such that the cap 508 is biased toward the adjustment mechanism 514, or toward a closed position. As a user exhales into the inlet 504, pressure within the interior chamber 503 of the housing 502 begins to build, and the force acting on the cap 508 resulting from such pressure increases. When a threshold pressure is reached, the force acting on the cap 508 resulting from the increased pressure in the interior chamber 503 of the housing 502 surpasses the biasing force acting on the cap 508 as a result of the magnetic attraction between the pair of magnets 512a and 512b, the cap 508 begins to open. As the cap 508 opens, the distance between the magnets 512a and 512b increases, leading to a rapid decay in magnetic attraction force, and allowing the cap 508 to burst open. In an open position, shown in FIG. 20, the exhaled air in the interior chamber 503 of the housing 502 and air in a user's airways is free to move through the device 500 between the inlet 504 and the outlet 506. This sudden release of built up pressure in the device 500 and in the user's airways translates to high velocity airflow through the user's airways that simulates a Huff Cough.

In an open position, a user may press and rotate the cap 508 to a closed position, as shown in FIG. 19. As the cap 508 is returned to a closed position, the pair of magnets 512a and 512b is moved in to proximity with one another, such that the cap 508 is biased toward the position shown in FIG. 19. The user may then repeat the above cycle.

Sixth Embodiment

FIGS. 21-25 show a sixth embodiment of a Huff Cough simulation device 600. In general, the device 600 includes a housing 602 having an interior chamber 603; an inlet 604 and an outlet 606; a piston 610; a pair of magnets 612a and 612b; and, an adjustment mechanism 614. The housing 602 is formed of an upper portion 615 and a lower portion 617 that may be removably attachable (e.g., by means of a snap-fit or threading), so that the components within the housing 602 may be periodically accessed for cleaning, replacement, or adjustment. Except for as described below, the structure and operation of the device 600 is otherwise the same as described above with regards to the device 100.

Figure 26A:
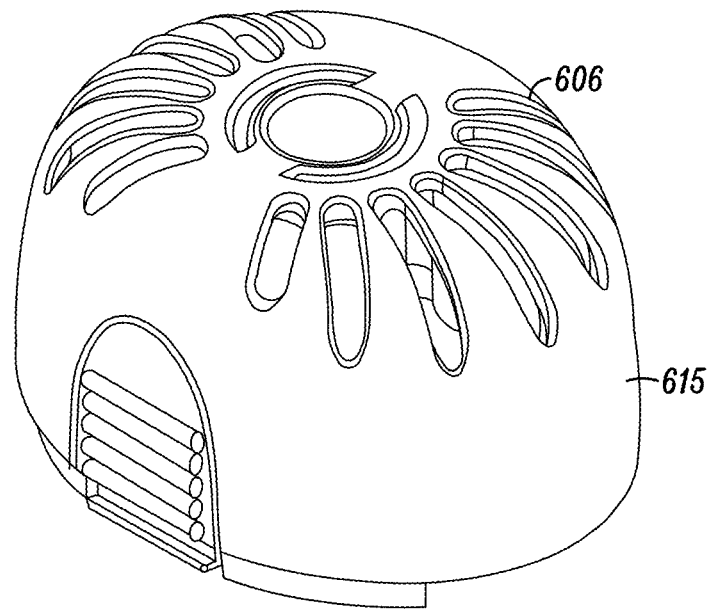
FIGS. 26A-26B are perspective and cross-sectional views of an upper portion of a housing of the Huff Cough simulation device of FIG. 21.
Figure 26B:
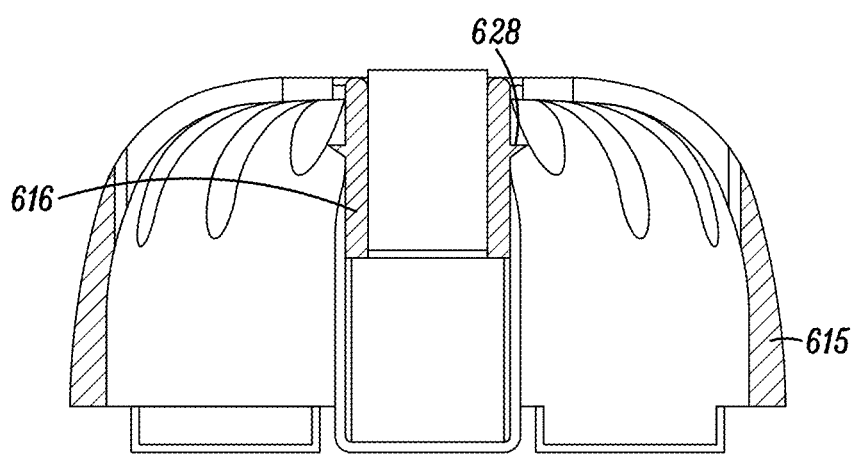

FIGS. 26A-26B are perspective and cross-sectional views of the upper portion 615 of the housing 602 of the device 600. As shown, the outlet 606 may comprise a plurality of openings in the upper portion 615 of the housing 602. Alternatively, the outlet 606 may comprise a single opening. As described further below, the upper portion 615 of the housing 602 also includes a catch or a groove 628 disposed on a cylindrical opening or slot 616 configured to retain the piston 610 in an open position.

Figure 23:
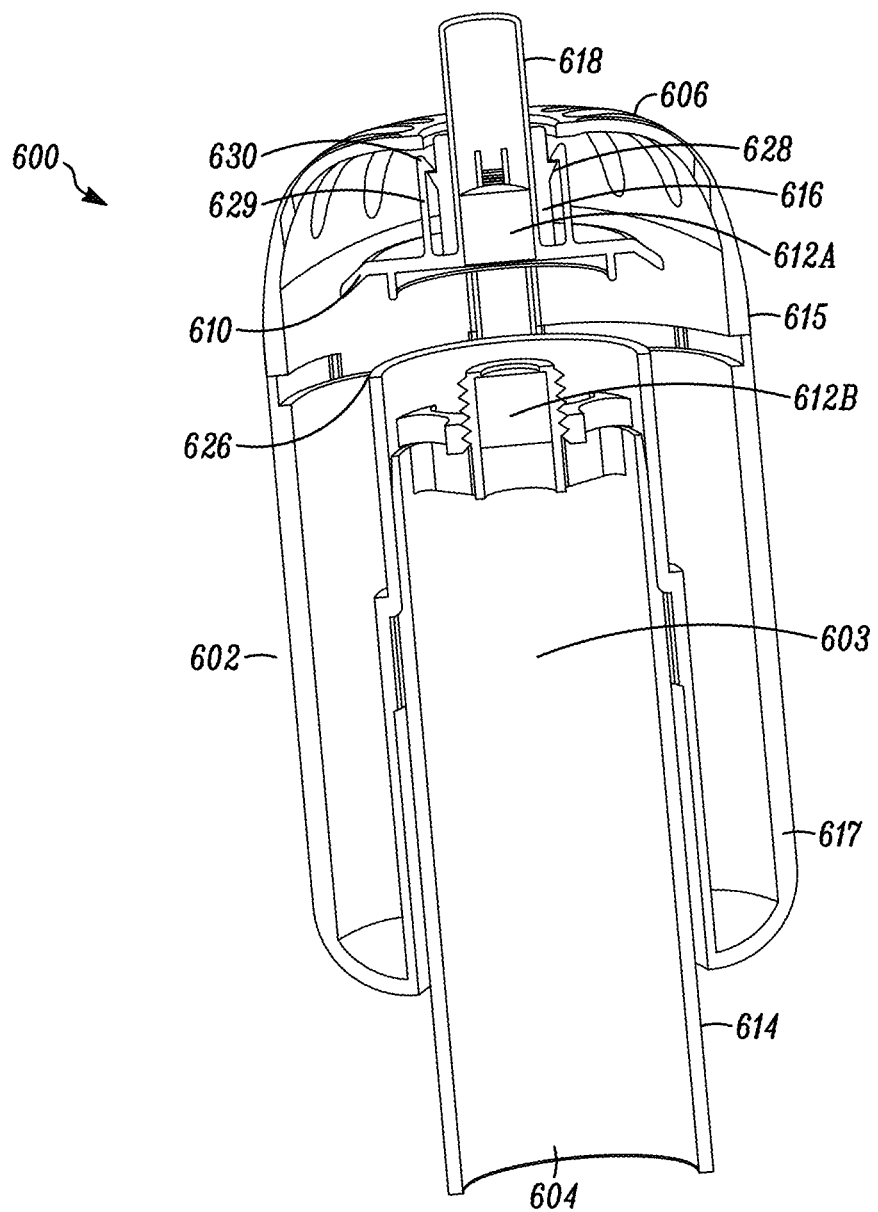
FIG. 23 is a cross-sectional perspective view of the Huff Cough simulation device of FIG. 21, showing the device in an open position.
Figure 24:
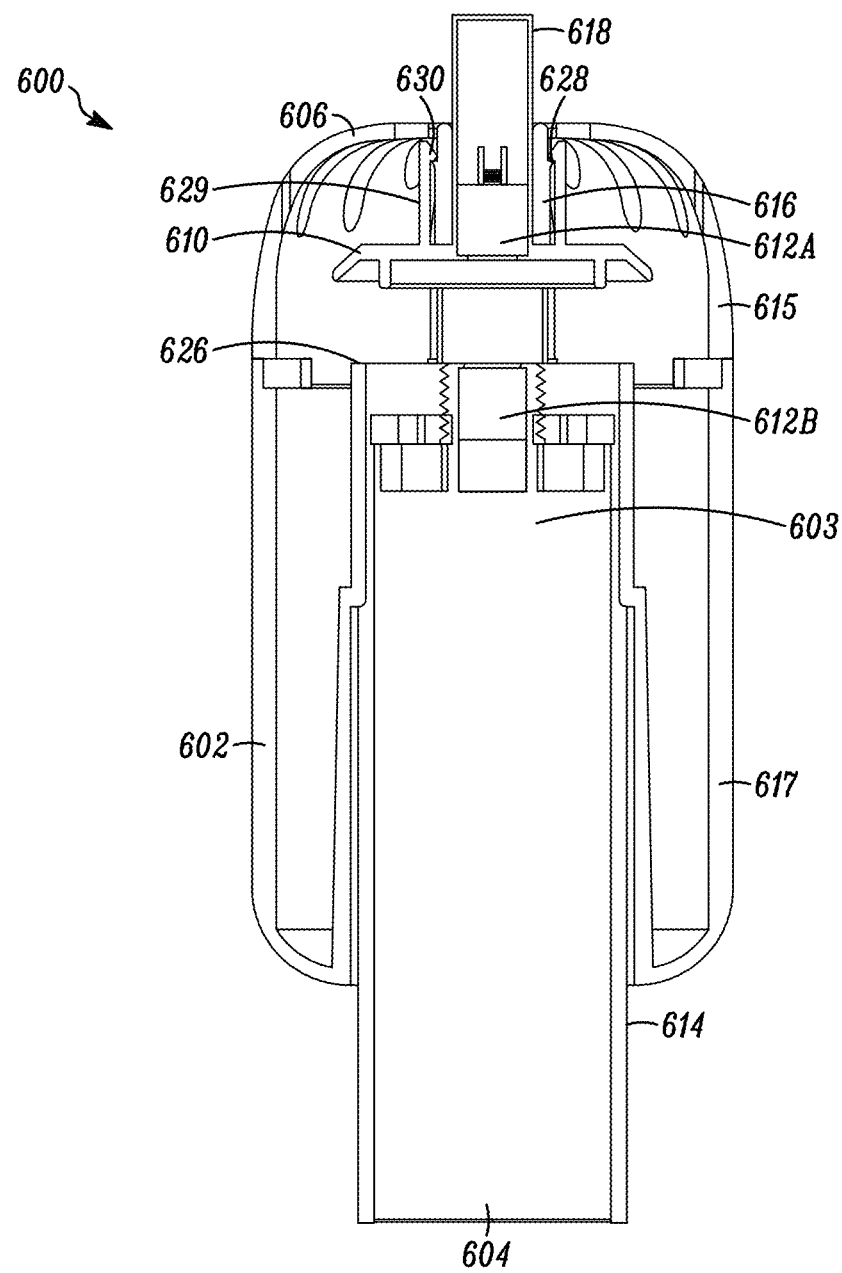
FIG. 24 is a cross-sectional side view of the Huff Cough simulation device of FIG. 21, showing the device in an open position.
Figure 25:
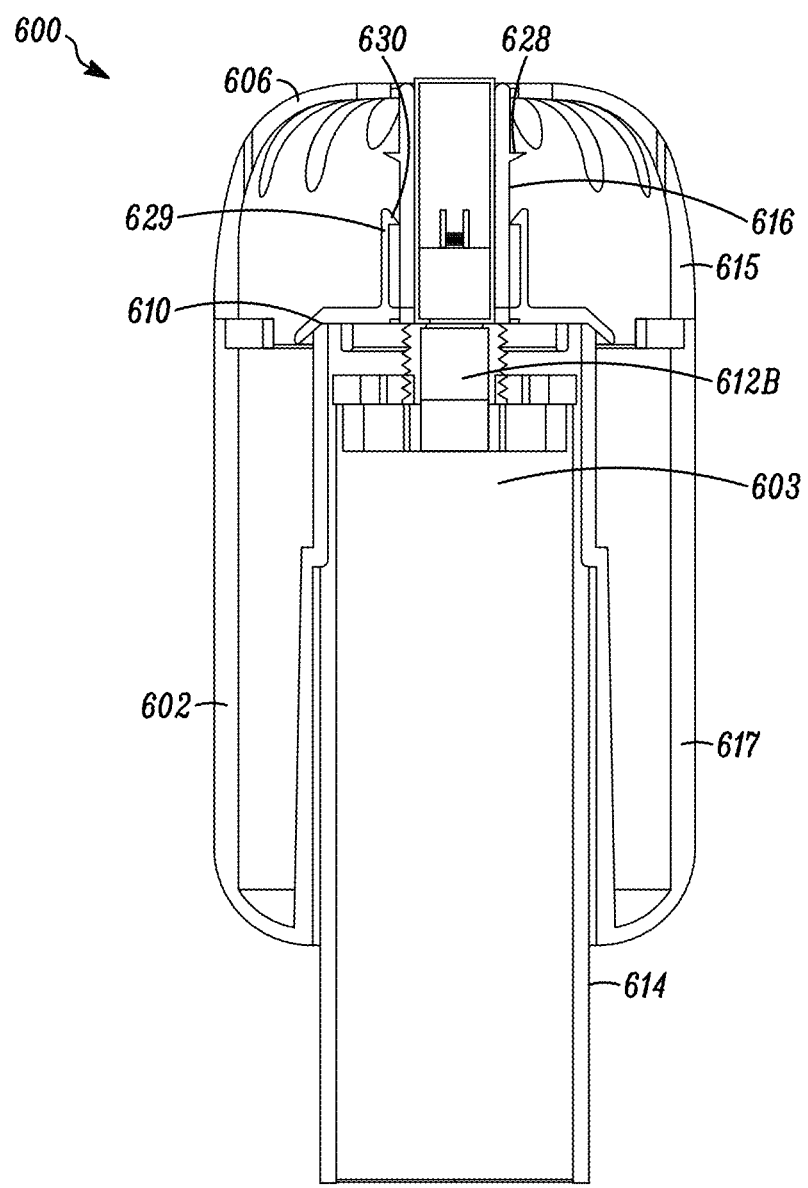
FIG. 25 is a cross-sectional side view of the Huff Cough simulation device of FIG. 21, showing the device in a closed position.
Figure 27A:
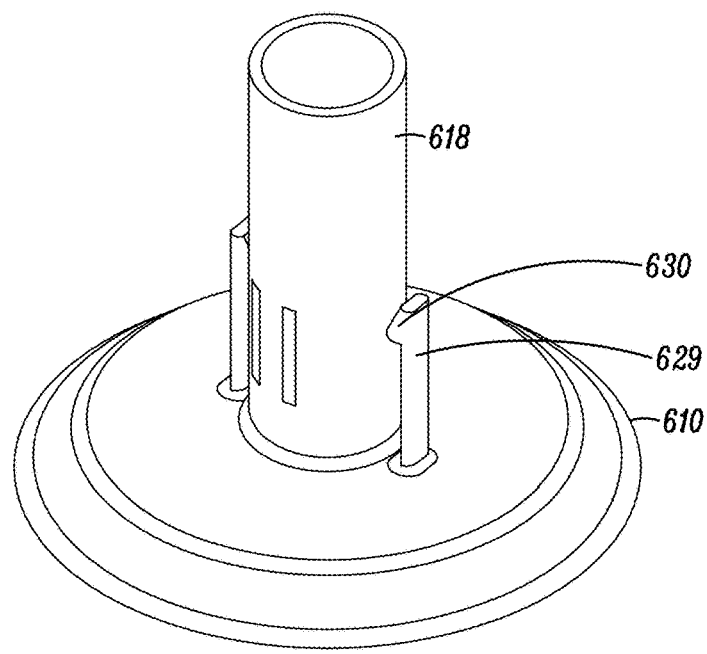
FIGS. 27A-27B are perspective and cross-sectional views of a piston of the Huff Cough simulation device of FIG. 21.
Figure 27B:
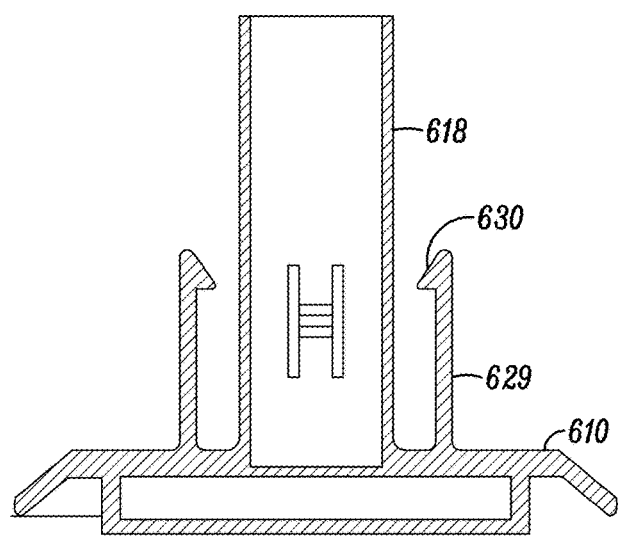

FIGS. 27A-27B are perspective and cross-sectional views of the piston 610 of the device 600. A shaft portion 618 extends from the piston 610 and is adapted to fit within the cylindrical opening or slot 616 of the upper portion 615 of the housing 602. As shown in FIGS. 23-25, the shaft portion 618 is also adapted to hold one magnet 612a of the pair of magnets. The piston 610 also comprises a pair of arms 629 that extend toward the upper portion 615 of the housing 602 and include a ridge or protrusion 630 configured to engage the catch or a groove 628 on the upper portion 615 of the housing 602, the combination of which operate as a mechanical latch that can retain the piston 610 in an open position shown in FIGS. 23-24 The bottom surface of the piston 610 may also operate as a blunt object placed in the flow path such that the flow of exhaled air must flow around this surface, preventing any mucus or secretions from flying out of the device, as they will impact this surface instead.

Figure 28A:
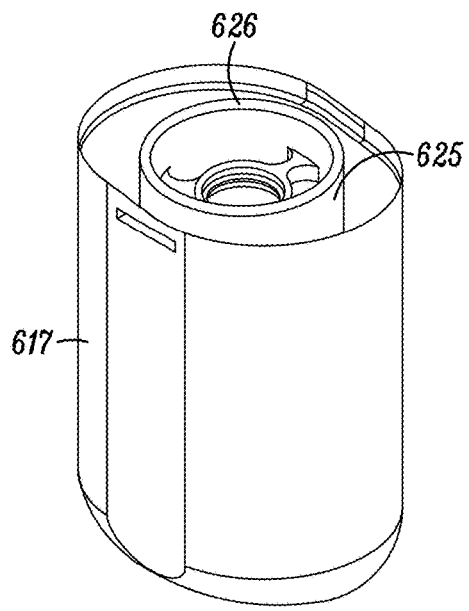
FIGS. 28A-28B are perspective and cross-sectional views of a lower portion of a housing of the Huff Cough simulation device of FIG. 21.
Figure 28B:
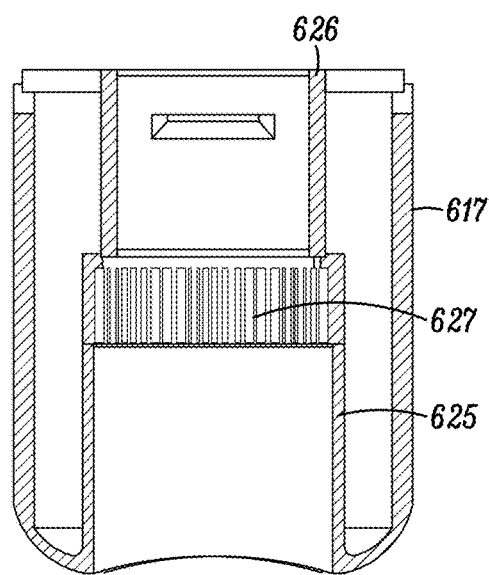
Figure 28C:
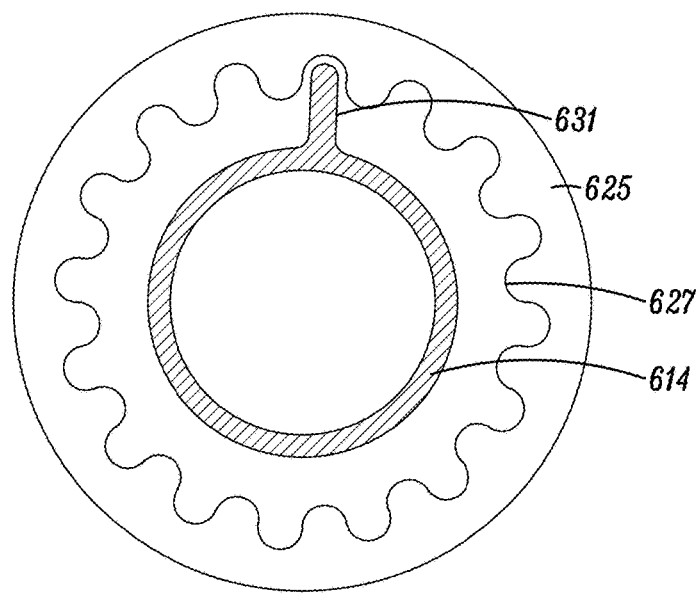
FIG. 28C is an illustration of the adjustment mechanism of the Huff Cough simulation device of FIG. 21

FIGS. 28A-28B are perspective and cross-sectional views of the lower portion 617 of the housing 602 of the device 600. In general, the lower portion 617 comprises a cylindrical opening or slot 625 adapted to receive the adjustment mechanism 614. As shown in FIGS. 28B-C, the interior surface of the cylindrical opening or slot 625 also includes a plurality of radial detents 627 configured to provide the adjustment mechanism 614 with discrete settings for fine control of the desired threshold pressure required to move the piston 610 from a closed position to an open position.

FIGS. 29A-29B are perspective and cross-sectional views of the adjustment mechanism 614 of the device 600. The adjustment mechanism 614 includes a shaft portion 624 that extends into the housing 602. As shown, the shaft portion 624 is adapted to hold one magnet 612b of the pair of magnets. In this embodiment, the adjustment mechanism also defines the inlet 604 and at least part of the interior chamber 603. A distal end of the shaft portion 624 is threaded, such that the adjustment mechanism 614 may be selectively rotated relative to the housing 602 to thereby advance or retract the shaft portion 624 and the magnet 612b within the housing 602. The adjustment mechanism also includes a finger 631 adapted to engage and rotate relative to the plurality of radial detents 627, similar to a "ratcheting" type of motion.

Figures 21, 22:
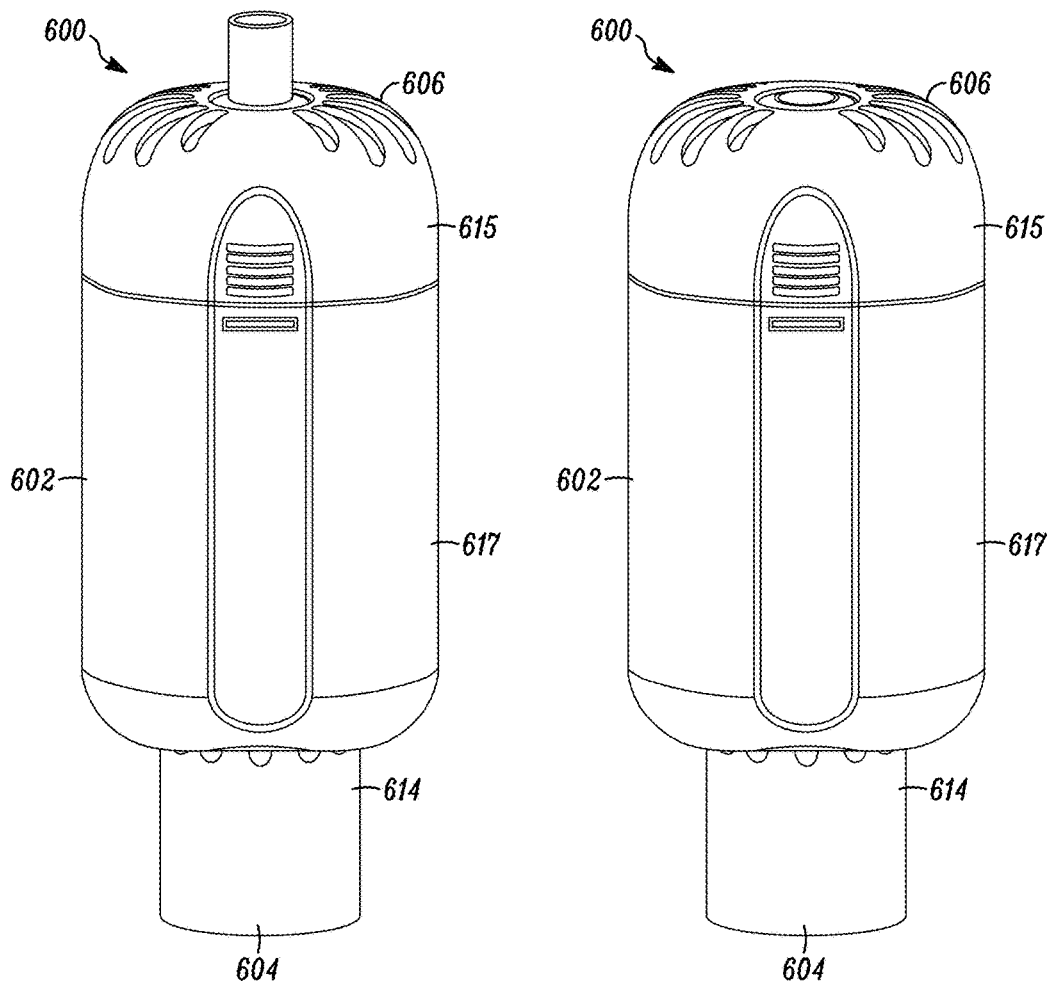
FIG. 21 is a perspective view of a sixth embodiment of a Huff Cough simulation device, showing the device in an open position.
FIG. 22 is a perspective view of the Huff Cough simulation device of FIG. 21, showing the device in a closed position.

When the device 600 is used as described above with regards to the device 100, and a threshold pressure is reached in the interior chamber 603 of the housing 602, the piston 610 is rapidly driven from a closed position, as shown in FIGS. 22 and 25, to an open position, as shown in FIGS. 21 and 23-24. As the piston 610 moves to an open position shown in FIGS. 21 and 23-24, the ridge or protrusion 630 on the pair of arms 629 on the piston 610 engages the catch or groove 628 on the upper portion 615 of the housing 602, such that the piston 610 is retained in an open position, as shown FIGS. 21 and 23-24. In this position, the shaft portion 618 of the piston 610 extends beyond the upper portion 615 of the housing 602, such that a user may push the shaft portion 618 of the piston 610 back into the housing 602, returning the piston 610 to a closed position. As the piston is returned to a closed position, the pair of magnets 612a and 612b is moved in to proximity with one another, such that the piston 610 is biased toward the adjustment mechanism 614 and in engagement with the ledge 626. The user may then repeat the above cycle.

FIG. 30 is a cross-sectional side view of an alternative embodiment of the device 600. In this alternative embodiment, one magnet 612b of the pair of magnets is replaced with a galvanized screw 612c having a ferrous core. The screw 612c may be threaded into the shaft portion 624 of the adjustment mechanism 614 such that the threads of the screw may be used for adjustment in the same manner as described above with reference to the device 100. In contrast to the embodiment described above with a pair of magnets 612a and 612b, which requires careful alignment of the magnets 612a and 612b to obtain the desired magnetic forces, this alternative embodiment creates a magnetic attraction regardless of the orientation of the screw 612c. The screw 612c is galvanized (e.g., with a thin layer of zinc) to minimize corrosion or oxidation while maintaining the magnetic properties of the ferrous core. Other types of coatings may also be used to prevent corrosion or oxidation, such as an epoxy.

While not shown, it is also envisioned that a one-way inhalation valve could be installed on the mouthpiece and configured to open upon inhalation, while remaining closed on exhalation, thereby allowing the user to repeatedly perform Huff Cough simulation on exhalation, then inhale, all without removing the device 600 from the user's mouth between breaths.

Seventh Embodiment

Figure 31:
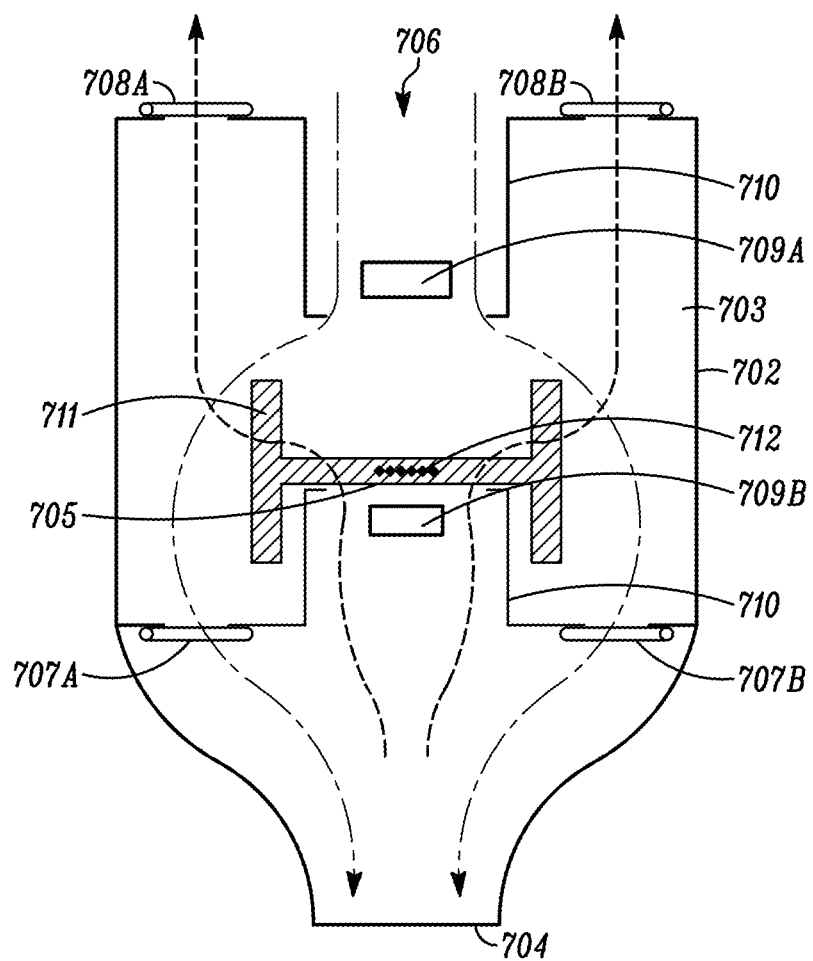
FIG. 31 is an illustration of a seventh embodiment of a Huff Cough simulation device.

FIG. 31 is an illustration of a seventh embodiment of a Huff Cough simulation device 700, showing a cross-sectional view of the device 700. As described below, the device 700 is adapted to be reset by means of the user's inhalation (e.g., returning the shuttle 711 from an open position to a closed position).

In general, the device 700 includes a housing 702 having an interior chamber 703, a mouthpiece 704, an inlet 705, an outlet 706, a pair of one-way inhalation valves 707a and 707b, a pair of one-way exhalation valves 708a and 708b, a pair of magnets 709a and 709b, a guide post 710, and a shuttle 711.

An exemplary flow path of air exhaled from a user into the mouthpiece 704 is shown in FIG. 31 as a uniform dashed line. An exemplary flow path of air inhaled by a user through the mouthpiece 704 is shown in FIG. 31 as a non-uniform dashed line. The one-way exhalation valves 708a and 708b are configured to open upon exhalation of air into the chamber 703, thereby letting air within the interior chamber 703 exit the housing 702, while at the same time, the one-way inhalation valves 707a and 707b remain closed. The one-way inhalation valves 707a and 707b are configured to open upon inhalation, thereby letting air within the interior chamber 703 exit the housing 702 through the mouthpiece 704, while at the same time, the one-way exhalation valves 708a and 708b remain closed.

The shuttle 711 is shaped and sized to move along the guide post 710 between a closed position (shown in FIG. 31) and an open position (not shown). The shuttle 711 includes an insert 712 having a ferrous core subject to magnetic attraction, e.g., from the pair of magnets 709a and 709b.

Operation of the Huff Cough simulation device 700 will now be described. Administration of treatment using the device 700 begins with the shuttle 711 in a closed position, for example, as shown in FIG. 31. In this position, the shuttle 711 is biased toward the closed position by the magnetic force attracting the insert 712 of the shuttle 711 toward the magnet 709b. As a user exhales into the mouthpiece 704, the one way inhalation valves 707a and 707b remain closed, while the flow of air through the inlet 705 is blocked by the shuttle 711. As a user continues to exhale, pressure within the mouthpiece 704 begins to build. When the force on the shuttle 711 as a result of the increased pressure in the mouthpiece 704 exceeds the magnetic force attracting the insert 712 toward the magnet 709b, the shuttle 711 begins to move along the guide post 710 toward the magnet 709a. As the shuttle 711 moves away from the magnet 709b toward the magnet 709a, the magnetic force between the shuttle 711 and the magnet 709b rapidly decreases, the magnetic force between the shuttle 711 and the magnet 709a rapidly increases, and the exhaled air within the mouthpiece flows rapidly through the inlet 705, into the interior chamber 703. While the shuttle 711 is moving toward the magnet 709a, some of the exhaled air may exit the interior chamber 703 through the outlet 706.

The magnetic force attracting the insert 712 of the shuttle 711 toward the magnet 709a moves the shuttle 711 into an open position (not shown), where the flow of air through the outlet 706 is blocked by the shuttle 711. In this position, exhaled air entering the interior chamber 703 through the mouthpiece 704 is allowed to exit the housing 702 through the one-way exhalation valves 708a and 709b, until the period of exhalation concludes.

The process is then reversed during a period of inhalation. In the open position (not shown), the flow of air through the outlet 706 is blocked by the shuttle 711. The shuttle 711 is biased toward the open position by the magnetic force attracting the insert 712 of the shuttle 711 toward the magnet 709a. As a user inhales through the mouthpiece 704, the one way exhalation valves 708a and 708b remain closed, while the flow of air through the outlet 706 is blocked by the shuttle 711. As a user continues to inhale, pressure within the interior chamber 703 begins to drop, such that a negative pressure is reached. When the force on the shuttle 711 as a result of the negative pressure in the interior chamber 703 exceeds the magnetic force attracting the insert 712 toward the magnet 709a, the shuttle begins to move along the guide post 710 toward the magnet 709b. In this embodiment, the negative pressure necessary to move the shuttle 711 from the open position to the close position is far less in magnitude than the positive pressure necessary to move the shuttle 711 from the closed position to the open position during exhalation. As the shuttle 711 moves away from the magnet 709a toward the magnet 709b, the magnetic force between the shuttle 711 and the magnet 709a rapidly decreases, the magnetic force between the shuttle 711 and the magnet 709b rapidly increases, and air surrounding the device 700 flows rapidly through the outlet 705, into the interior chamber 703. While the shuttle 711 is moving toward the magnet 709b, some of the air in the interior chamber 703 may be inhaled through the inlet 705.

The magnetic force attracting the insert 712 of the shuttle 711 toward the magnet 709b moves the shuttle 711 back into a closed position (shown in FIG. 31), where the flow of air through the inlet 705 is blocked by the shuttle 711. In this position, inhaled air entering the interior chamber 703 through the outlet 706 is allowed to pass through the housing 702 through the one-way inhalation valves 707a and 707b, until the period of inhalation concludes. When a period of exhalation resumes, the process described above is repeated.

Eighth Embodiment

FIGS. 32-35 are illustrations of an eighth embodiment of a Huff Cough simulation device 800. As descried herein, the device 800 utilizes vacuum pressure to perform Huff Cough therapy. The use of a vacuum has the added benefit of exposing a user's airways to a negative pressure at the moment air flow begins (i.e., when the seal first opens). This negative pressure increases the pressure differential from inside the user's lungs to the outside atmosphere, which in turn results in higher air velocities in the user's airways, and therefore even higher shear forces on secretions lining the airways.

As described herein, the vacuum utilized with the device 800 may be selected from any number of available commercial devices. For example, the vacuum could comprise an electric pump. Alternatively, a trigger or squeeze mechanism connected to a one-way valve could be used, similar to those used on manual breast pumps. Regardless of its form, the amount of vacuum may be selected to define the threshold exhalation pressure required to break the seal.

As shown in FIGS. 32-35, the device 800 generally comprises a housing 802 enclosing a chamber 803, a mouthpiece 804, an inlet 805, an outlet 806, a sealing member 807 having an inlet seal 808 and an outlet seal 809, a vacuum 810 in communication with the interior chamber 803, a gauge 811, and a one-way valve 812 configured only to let air exit the interior chamber 812 . The sealing member 807 is rotatably mounted to the housing 802, and is biased, e.g., by a torsion spring (not shown), toward a closed position, where the inlet seal 808 prevents the flow of air through the inlet 805, and the outlet seal 809 prevents the flow of air through the outlet 806.

Operation of the Huff Cough simulation device 800 will now be described. Administration of treatment using the device 800 begins, as shown in FIG. 32, with the sealing member 807 in a closed position, where the flow of air through the inlet 805 is prevented by the inlet seal 808, and flow of air through the outlet 806 is prevented by the outlet seal 809. A closing biasing force, or a moment ($M_s$), holds the sealing member 807 in the closed position. The interior chamber 803 is not pressurized.

As shown in FIG. 33, the vacuum 810 is then used to pressurize the interior chamber 803 to the desired negative pressure, which is indicated on the gauge 811. In this state, the negative pressure causes a force ($F_{v1}$) to act on the inlet seal 808 and a force ($F_{v2}$) to act on the outlet seal 809. Because the outlet 806 has a greater cross-sectional area than the inlet 805, the force ($F_{v2}$) acting on the outlet seal 809 as a result of the negative pressure is greater than the force ($F_{v1}$) acting on the inlet seal 808 as a result of the negative pressure. As a result, an additional moment ($M_v$)

that is proportional to the negative pressure is created that also biases the sealing member 807 toward the closed position.

Figures 34, 35:
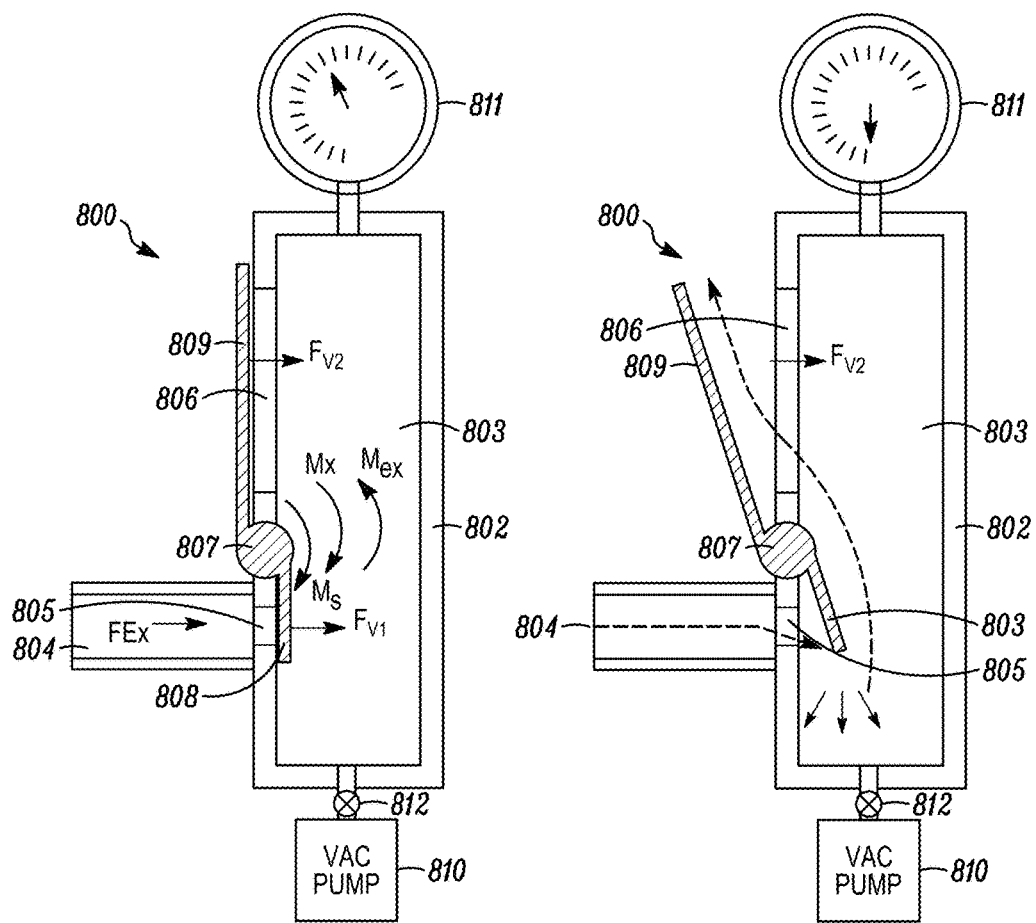
FIG. 34 is an illustration of the Huff Cough simulation device of FIG. 32, showing the device pressurized and in a closed position during a period of exhalation; and, FIG. 35 is an illustration of the Huff Cough simulation device of FIG. 32, showing the device in an open position during a period of exhalation.

When a user exhales into the mouthpiece 804, as shown in FIG. 34, a positive pressure begins to build in the mouthpiece 804. As a result of the increased pressure in the mouthpiece 804, a force ($F_{EX}$) acts on the inlet seal 808, thereby creating a moment ($M_{EX}$) biasing the sealing member 807 toward an open position. The sealing member 807 remains in the closed position until the opening moment ($M_{EX}$) exceeds the sum of the moment ($M_s$) generated by the spring and the moment ($M_v$) created by the negative pressure in the interior chamber 803.

As shown in FIG. 35, the sealing member 807 moves to an open position when the opening moment ($M_{EX}$) exceeds the sum of the moment ($M_s$) generated by the spring and the moment ($M_v$) generated by the negative pressure in the interior chamber 803. When the sealing member 807 moves to an open position, the outlet 806 is no longer blocked by the outlet seal 809, and the inlet 805 is no longer blocked by the inlet seal 808, thereby permitting exhaled air to travel rapidly through the mouthpiece and inlet 805 into the interior chamber 803, then exit the interior chamber 803 through the outlet 806. When the moment ($M_s$) acting on the sealing member 807 as a result of the closing biasing force (e.g., by a torsion spring) overcomes any opening moment ($M_{EX}$) as a result of exhaled air traveling through the device 800, the sealing member 807 returns to a closed position, as shown in FIG. 32. The process of above may then be repeated during subsequent periods of exhalation.

While not shown, it is also envisioned that a one-way inhalation valve could be installed on the mouthpiece and configured to open upon inhalation, while remaining closed on exhalation, thereby allowing the user to repeatedly perform Huff Cough simulation on exhalation, then inhale, all without removing the device 800 from the user's mouth between breaths.

It should be appreciated that the various modifications and alternatives described herein with regards to a particular embodiment may also be applied to the other embodiments described herein.

The foregoing description of the embodiments has been presented for purposes of illustration and description, and is not intended to be exhaustive or to limit the inventions to the precise forms disclosed. It will be apparent to those skilled in the art that the present inventions are susceptible of many variations and modifications coming within the scope of the following claims.

What is claimed is:

1. A respiratory treatment device comprising:
   an inlet configured to receive exhaled air into the device;
   an outlet configured to permit exhaled air to exit the device;
   a blocking member moveable between a closed position where a flow of air through the device is restricted, and an open position where the flow of air through the device is less restricted than where the blocking member is in the closed position; and,
   a biasing member comprising a pair of magnets configured to bias the blocking member toward the closed position, wherein a level of bias decreases as the blocking member moves from the closed position to the open position;
   wherein a distance between a first magnet and a second magnet of the pair of magnets is selectively adjustable when the blocking member is in the closed position.

2. The respiratory treatment device of claim 1, wherein the blocking member moves from the closed position to the open position in response to a threshold exhalation pressure in the device.

3. A respiratory treatment device comprising:
   an inlet configured to receive exhaled air into the device;
   an outlet configured to permit exhaled air to exit the device;
   a blocking member moveable between a closed position where a flow of air through the device is restricted, and an open position where the flow of air through the device is less restricted than where the blocking member is in the closed position; and,
   a biasing member configured to maintain the blocking member in the closed position until a threshold exhalation pressure is reached in the device;
   wherein, the blocking member is maintained in the open position once the blocking member moves to the open position, when there is no flow of exhaled air through the device.

4. The respiratory treatment device of claim 3, wherein the blocking member is moveable form the open position to the closed position by a user.

5. The respiratory treatment device of claim 3, wherein a level of bias decreases as the blocking member moves from the closed position to the open position.

6. The respiratory treatment device of claim 3, wherein the biasing member comprises a pair of magnets.

7. The respiratory treatment device of claim 3, wherein a distance between a first magnet and a second magnet of the pair of magnets is selectively adjustable when the blocking member is in the closed position.

8. The respiratory treatment device of claim 3, wherein the blocking member moves from the closed position to the open position in response to a threshold exhalation pressure in the device.

9. A respiratory treatment device comprising:
   a housing enclosing a chamber;
   an inlet configured to receive air into the chamber;
   an outlet configured to permit air to exit the chamber;
   a vacuum generator in communication with the chamber, the vacuum being configured to generate a negative pressure in the chamber; and,
   a sealing member moveable relative to the inlet and the outlet between a closed position where a flow of air through the inlet and the outlet is restricted, and an open position where the flow of air through the inlet and the outlet is less restricted than where the sealing member is in the closed position;
   wherein the sealing member is biased toward the closed position by the negative pressure in the chamber; and,
   wherein the sealing member is configured to move from the closed position to the open position when an exhalation pressure at the inlet is sufficient to overcome the bias on the sealing member by the negative pressure in the chamber.

10. The respiratory treatment device of claim 9, wherein the sealing member is rotatably mounted to the housing.

11. The respiratory treatment device of claim 9, wherein a cross-sectional area of the outlet is greater than a cross sectional area of the inlet.

12. The respiratory treatment device of claim 9, wherein the sealing member is biased by a spring toward the closed position.

13. The respiratory treatment device of claim 9, further comprising a mouthpiece in communication with the inlet, the mouthpiece having a one-way inhalation valve configured to open on inhalation and close on exhalation.

14. respiratory treatment device of claim 9, wherein the vacuum generator comprises an electric pump.

15. The respiratory treatment device of claim 9, further comprising a pressure gauge in communication with the chamber.

16. A respiratory treatment device comprising:
a housing enclosing a chamber;
an inlet configured to receive air into the chamber;
a first magnet positioned at the inlet;
an outlet configured to permit air to exit the chamber;
a second magnet positioned at the outlet;
a shuttle configured to move relative to the first magnet and relative to the second magnet between a closed position where a flow of air through the inlet is restricted by the shuttle, and an open position where a flow of air through the outlet is restricted by the shuttle;
wherein the shuttle is configured to move from the closed position to the open position when an exhalation pressure at the at the inlet is sufficient to overcome a magnetic attraction force between the shuttle and the first magnet; and,
wherein the shuttle is configured to move from the open position to the closed position when an inhalation pressure in the chamber is sufficient to overcome a magnetic attraction force between the shuttle and the second magnet.

17. The respiratory treatment device of claim 16, wherein the shuttle comprises an insert subject to magnetic attraction.

18. The respiratory treatment device of claim 16, wherein the first magnet is positioned in the inlet.

19. The respiratory treatment device of claim 16, wherein the second magnet is positioned in the outlet.

20. The respiratory treatment device of claim 16, further comprising a mouthpiece in communication with the inlet.

21. The respiratory treatment device of claim 20, further comprising a one-way inhalation valve configured to permit the flow of air through from the chamber into the mouthpiece.

22. The respiratory treatment device of claim 16, further comprising a one-way exhalation valve configured to permit the flow of air from the chamber out of the housing.

* * * * *